(12) United States Patent  
Tomono

(10) Patent No.: US 8,062,835 B2
(45) Date of Patent: Nov. 22, 2011

(54) METHOD OF MANUFACTURING MASTER PLATE, METHOD OF MANUFACTURING MICRONEEDLE PATCH AND APPARATUS EXPOSURE APPARATUS

(75) Inventor: Takao Tomono, Tokyo (JP)

(73) Assignee: Toppan Printing Co., Ltd., Tokyo (JP)

( * ) Notice: Subject to any disclaimer, the term of this patent is extended or adjusted under 35 U.S.C. 154(b) by 0 days.

(21) Appl. No.: 12/379,308

(22) Filed: Feb. 18, 2009

(65) Prior Publication Data

US 2009/0162798 A1   Jun. 25, 2009

Related U.S. Application Data

(63) Continuation of application No. PCT/JP2007/066043, filed on Aug. 17, 2007.

(30) Foreign Application Priority Data

Aug. 18, 2006 (JP) .................... 2006-223600
Aug. 18, 2006 (JP) .................... 2006-223602

(51) Int. Cl.
  *G03F 7/26* (2006.01)
  *A61M 3/00* (2006.01)
(52) U.S. Cl. ....................... 430/320; 604/272
(58) Field of Classification Search ........... 430/320; 264/220
  See application file for complete search history.

(56) References Cited

U.S. PATENT DOCUMENTS

| 4,444,616 | A | 4/1984 | Fujita et al. |
| 6,482,575 | B2 * | 11/2002 | Tokai et al. ............ 430/321 |
| 2002/0042025 | A1 | 4/2002 | Takai et al. |
| 2006/0055090 | A1 | 3/2006 | Lee et al. |
| 2007/0003839 | A1 | 1/2007 | Rabarot et al. |

FOREIGN PATENT DOCUMENTS

| JP | 57-200042 | 12/1982 |
| JP | 2001-235873 | 8/2001 |
| JP | 2001-356187 | 12/2001 |
| JP | 2002-8522 | 1/2002 |
| JP | 2002-096334 | * 4/2002 |
| JP | 2002-117756 | 4/2002 |
| JP | 2003-296975 | 10/2003 |
| JP | 2005-199392 | 7/2005 |
| JP | 2005-246595 | 9/2005 |
| JP | 2006-195168 | 7/2006 |
| WO | 2004/062899 A2 | 7/2004 |

(Continued)

OTHER PUBLICATIONS

International Search Report for PCT/JP2007/066043, mailed Oct. 30, 2007.

(Continued)

*Primary Examiner* — Kathleen Duda
*Assistant Examiner* — Caleen Sullivan

(57) ABSTRACT

A method of manufacturing a master plate includes the steps of forming a photoresist film on a substrate, disposing a photomask having a plurality of island radiation shields on the photoresist film followed by integrating the photomask and the photoresist film, applying light from a light source to the photoresist film through the photomask for selectively exposing the photoresist film, and developing the photoresist film to form a master plate, in which the method includes irradiating the photoresist film with the light from plural directions through the photomask to selectively expose the photoresist film from the respective directions.

7 Claims, 20 Drawing Sheets

FOREIGN PATENT DOCUMENTS

WO 2005/017623 A2 2/2005

OTHER PUBLICATIONS

Fabrication of microneedle array using inclined LIGA process, Moon, Sang-Jun and Seung S. Lee, Departments of Mechanical Engineering, Pohang University of Science and Technology, The 12$^{th}$ International Conference on Solid State Sensors, Actuators and Microsystems, Boston, Jun. 8-12, 2003(pp. 1546-1549).

Microfabricated needles for transdermal delivery of macromolecules and nanoparticles: Fabrication methods and transport studies, Devin V. McAllister, Ping M. Wang, Shawn P. Davis, Jung-Hwan Park, Paul J. Canatella, Mark G. Allen, and Mark R. Prausnitz, Nov. 25, 2003 (pp. 13755-13760).

A Novel Polymer Microneedle Arrays and PDMS Micromolding Technique. Shyn-Chyu Kuo and Yukon Chou, Electronics Research & Service Organization Industrial Technology Research Institute, Tamkang Journal of Science and Engineering, vol. 7, No. 2, pp. 95-98(2004).

International Preliminary Report on Patentability issued on Mar. 5, 2009 in corresponding International Patent Application PCT/JP2007/066043.

* cited by examiner

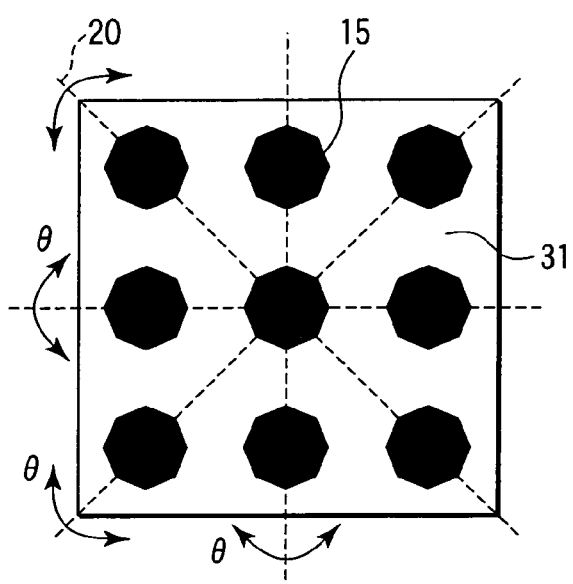
F I G. 6A
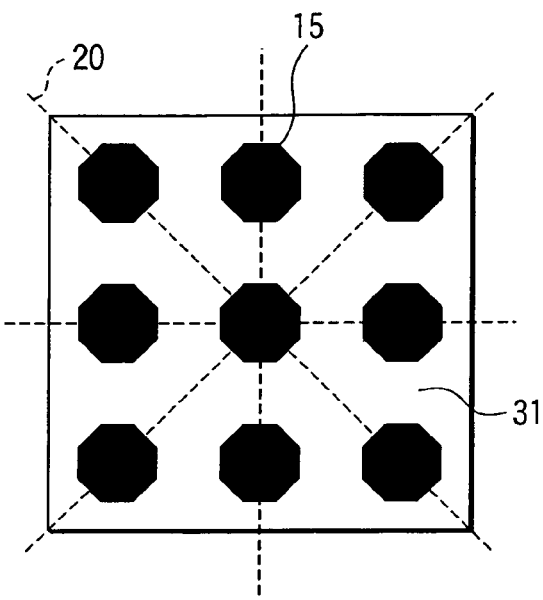
F I G. 6B
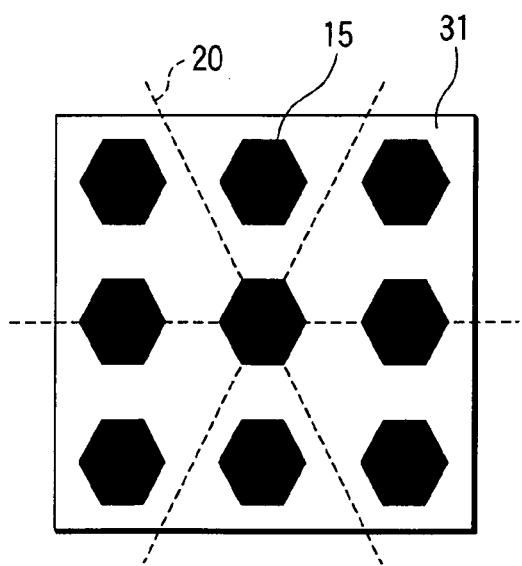
F I G. 6C
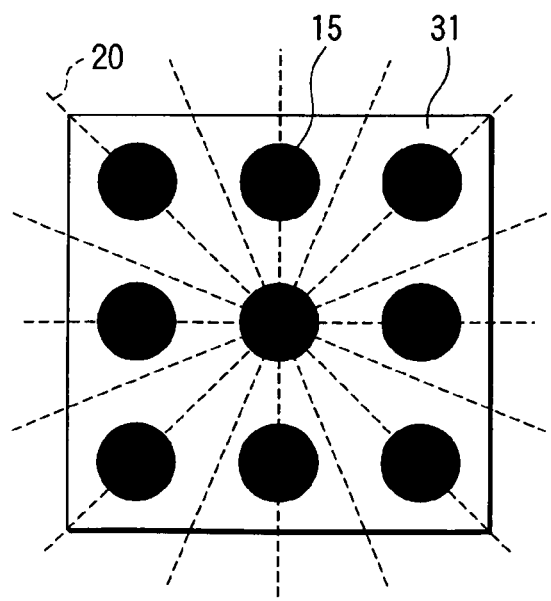
F I G. 6D

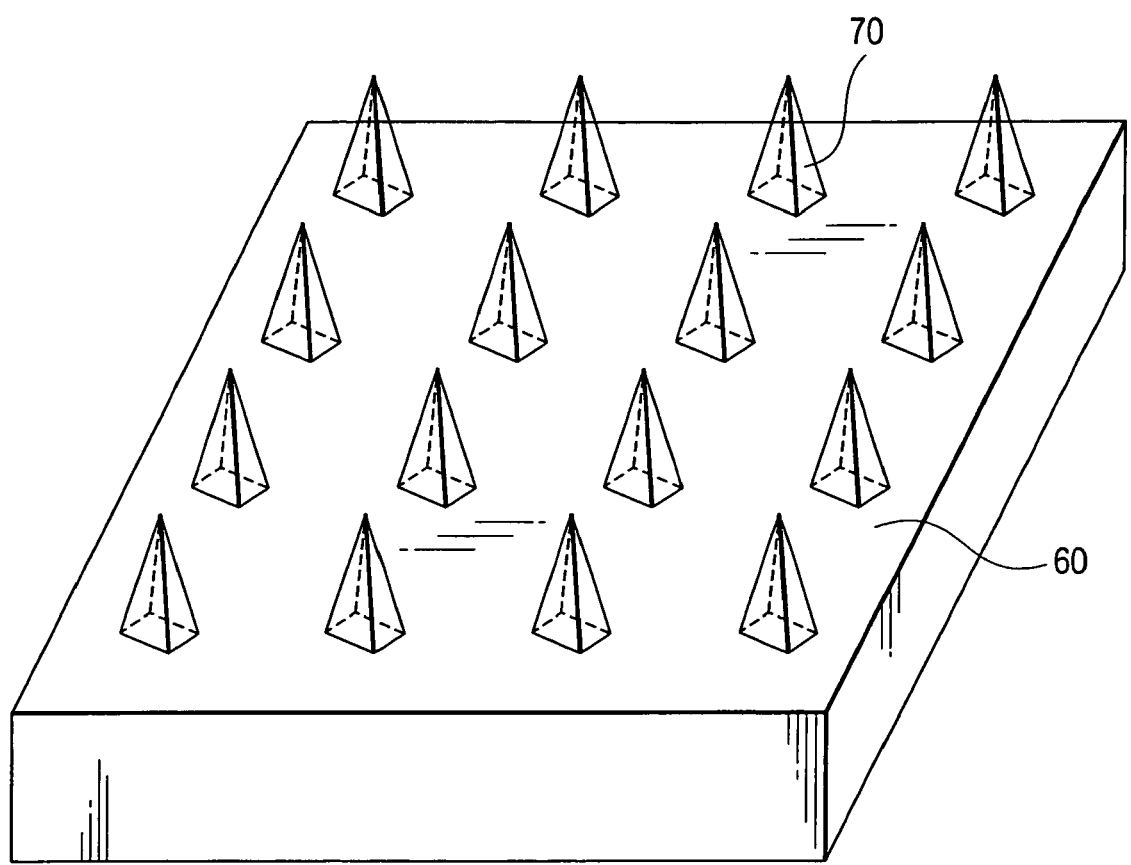
F I G. 10

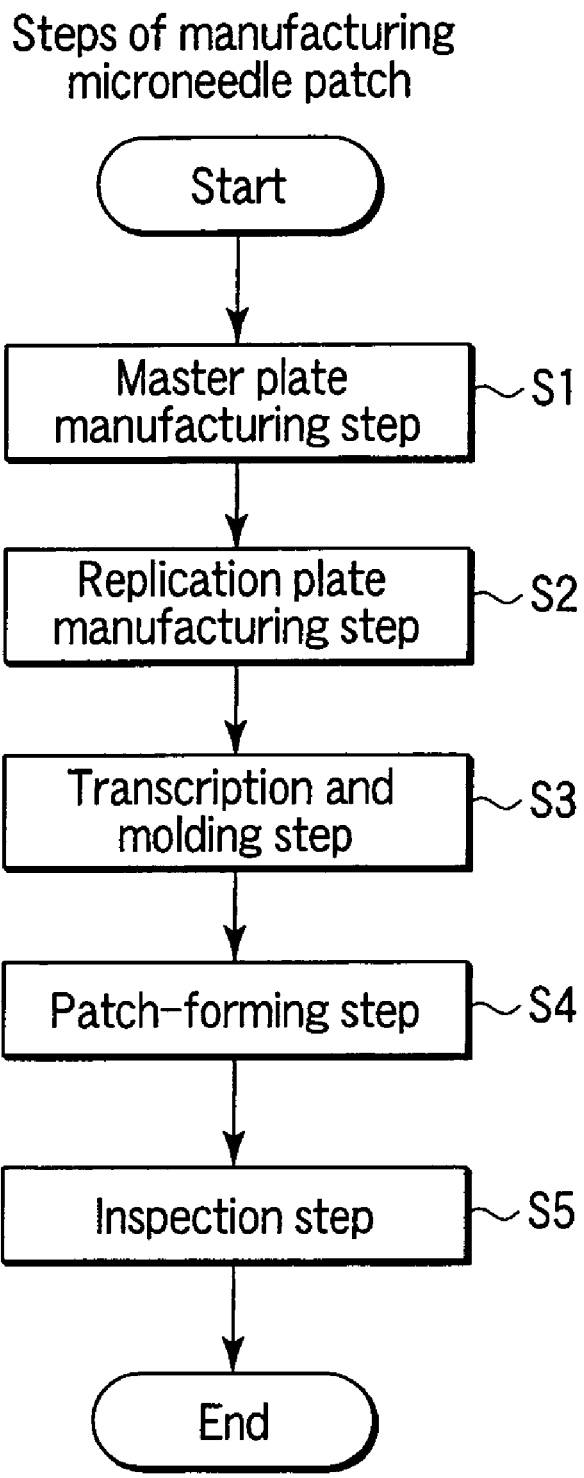
F I G. 11

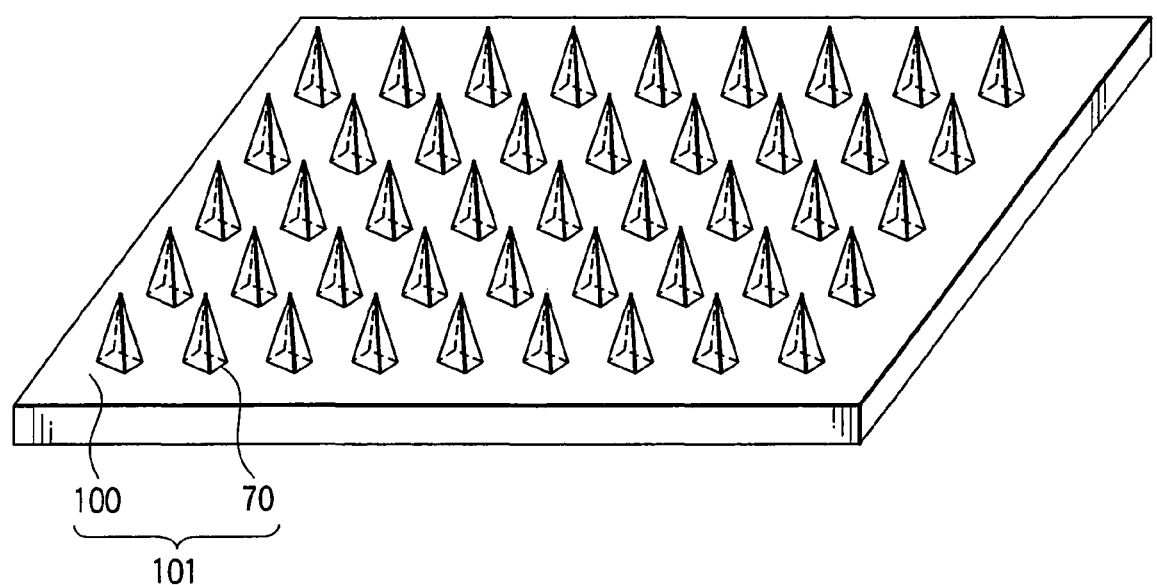
F I G. 13

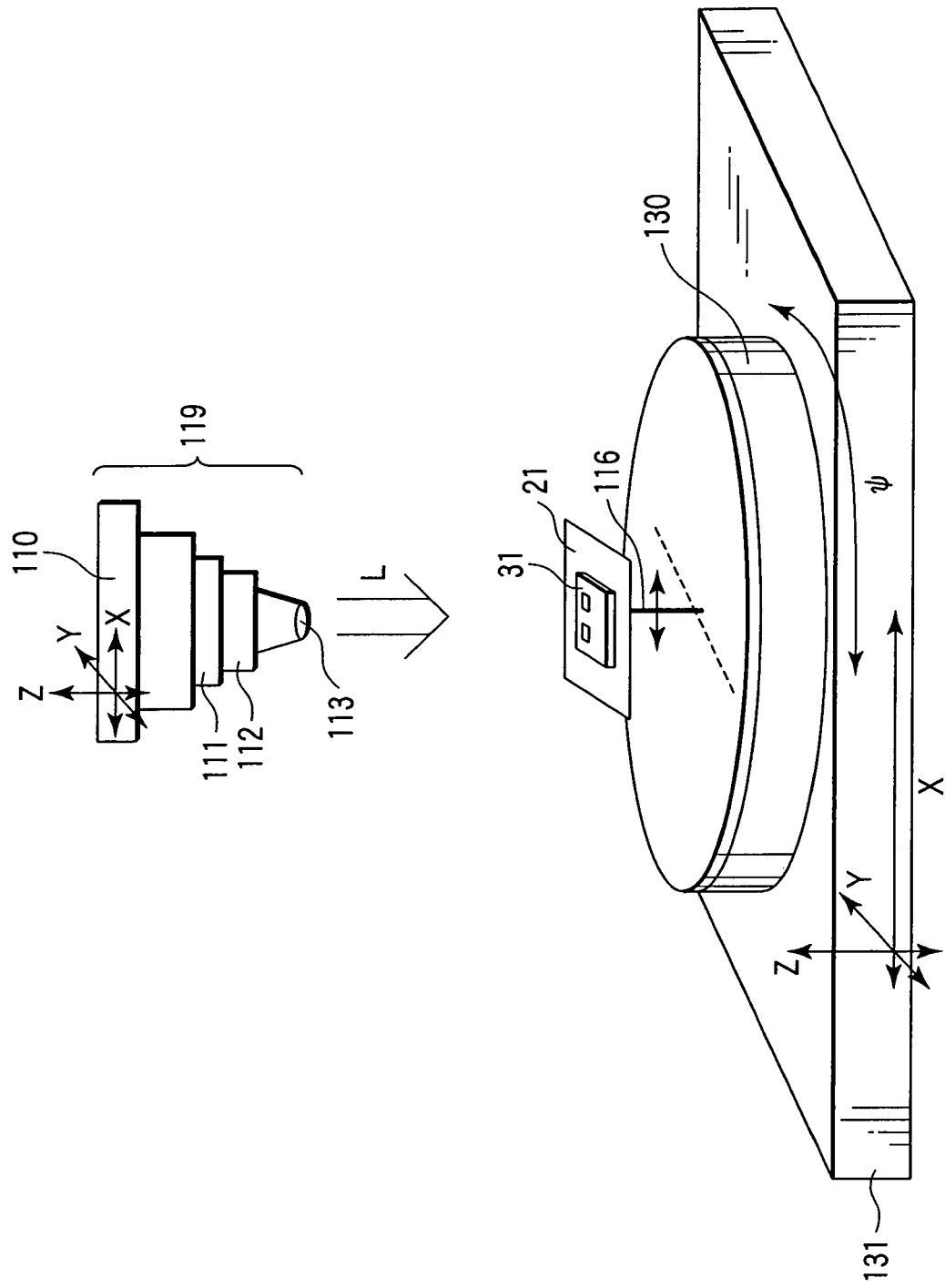
F I G. 16

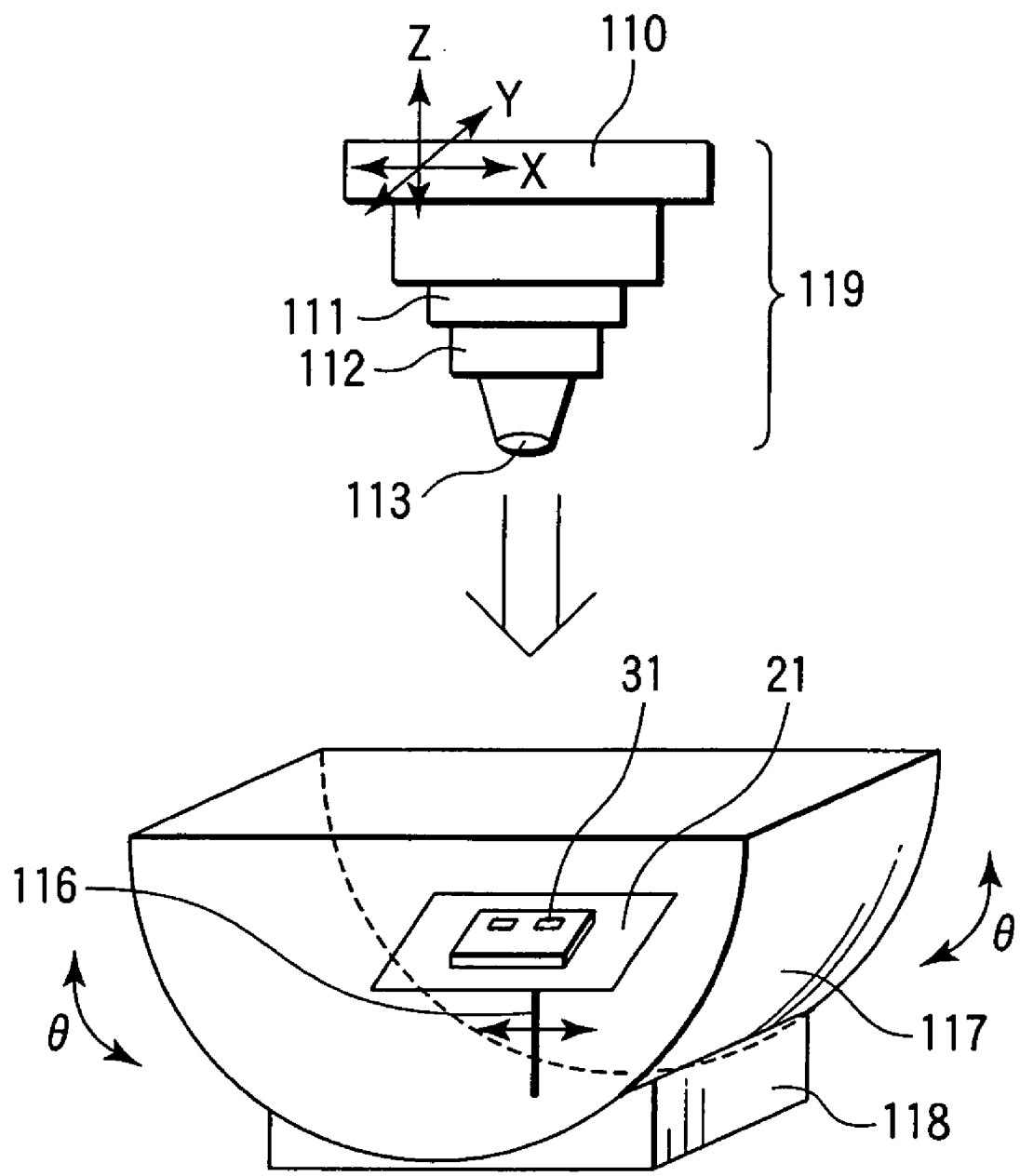
F I G. 17

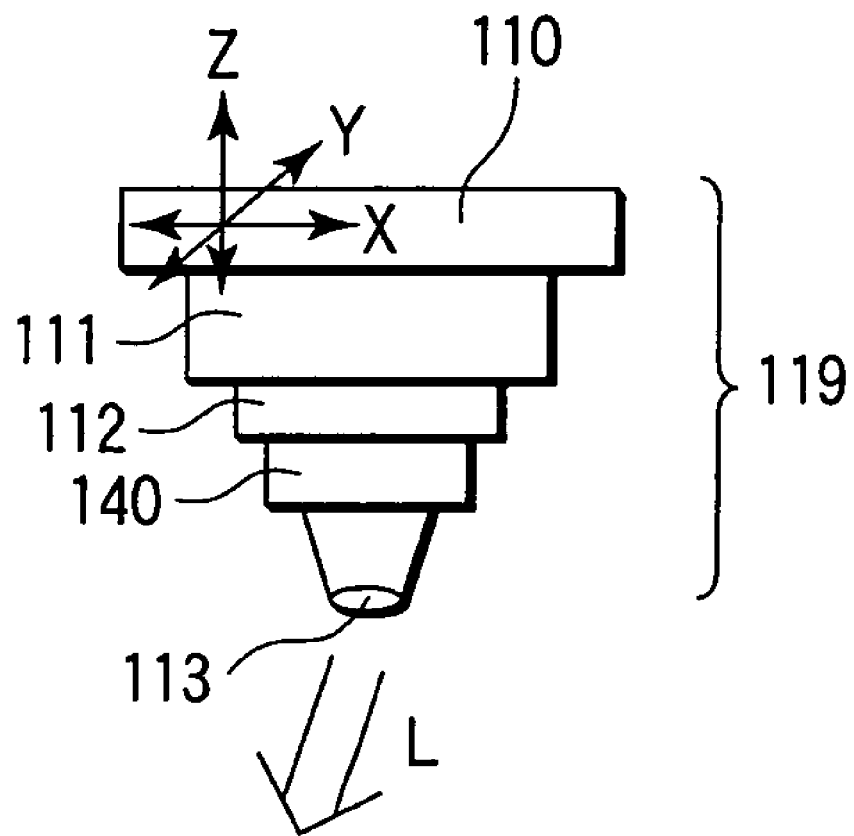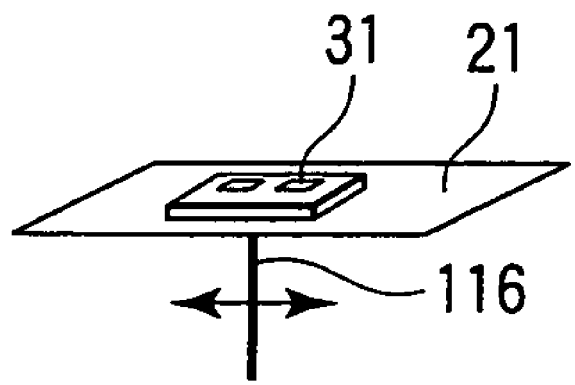
F I G. 18

METHOD OF MANUFACTURING MASTER PLATE, METHOD OF MANUFACTURING MICRONEEDLE PATCH AND APPARATUS EXPOSURE APPARATUS

CROSS REFERENCE TO RELATED APPLICATIONS

This is a Continuation Application of PCT Application No. PCT/JP2007/066043, filed Aug. 17, 2007, which was published under PCT Article 21(2) in Japanese.

This application is based upon and claims the benefit of priority from prior Japanese Patent Applications No. 2006-223600, filed Aug. 18, 2006; and No. 2006-223602, filed Aug. 18, 2006, the entire contents of both of which are incorporated herein by reference.

BACKGROUND OF THE INVENTION

1. Field of the Invention

The present invention relates to a method of manufacturing a master plate, a method of manufacturing a microneedle patch used as a tool for administering drugs to a specified layer in the skin, a microneedle patch and an exposure apparatus.

2. Description of the Related Art

A liquid drug has been usually applied on the skin for administering the drug through the surface of a living body such as the skin. Application of the drug to the skin is a non-invasive method, and is excellent in that the method gives no stress on a patient. However, the applied drug is easily removed by sweat or touch. Daily repeated application of the drug involves problems in terms of convenience and safety. It is another problem that control of permeability is not easy when the drug is to be permeated into the inner layer of the skin.

Under the circumstances, a microneedle having a transport function of the drug has been proposed. The microneedle may be used for transport of various substances such as sampling of the blood. Although a method of permitting the drug to infiltrate into the skin using microneedles or a microneedle patch on which the drug has been applied in advance is not a perfectly non-invasive application method of the drug, stimulation to the patient is relatively small since the drug is injected into a shallow region of the skin such as the epidermis using an ultra-fine microneedle. The drug may be infiltrated with high efficiency as compared with the method of applying the drug merely on the surface of the skin.

There is known a method of manufacturing a microneedle in which silicon is subjected to dry etching (Devin V. McAllister et al., PNAS, Nov. 25, 2003, vol. 100, No. 24, 13755-13760; Shyh-Chyi Kuo et al., Tamkang Journal of Science and Engineering, Vol. 7, No. 2, 95-98 (2004)).

While a quite fine and complicated planar pattern may be formed on the surface of a photoresist film or substrate by these methods, the three-dimensional shape obtained is columnar, and the depth of a recess to the surface is fixed to be constant. This is because, while the planar shape may be freely changed in accordance with a photomask, there was no method of freely forming the recess in a depth direction. Consequently, a cone shape such as a round cone and square cone cannot be formed, and it is difficult to apply the method of the manufacturing the microneedle. Since etching residues are left behind on the surface when the surface of the silicon microneedle is observed with an electron microscope, the surface is roughened due to the residues. Consequently, high surface roughness remains on a replication plate and on the microneedle manufactured using the silicon microneedle as a master plate.

It has been known to use a method referred to as LIGA (Lithographic, Galvanoformung and Abformung) to manufacture a microneedle (Moon, Sang-Jun et al., Transducers '03, 3E95.P (The 12th International Conference on Solid State Sensors, Actuators and Microsystems, Boston, Jun. 8-12, 2003; Jpn. Pat. Appln. KOKAI Publication No. 2005-246595).

The method of manufacturing the microneedle by LIGA involves the following steps. An X-ray sensitive photoresist such as a polymethyl methacrylic (PMMA) resin is applied on the substrate. Island radiation shields made of a material such as gold are applied on the resist, which is irradiated with X-ray having a high parallel nature. A three-dimensional structure made of PMMA is obtained upon development. A master plate is manufactured by electroforming of nickel on the three-dimensional structure. It is an advantage of this method that the tip of the microneedle may be sharpened with a smooth surface.

However, synchrotron radiation equipment that is large size equipment is necessary for the LIGA process. Accordingly, this method is inappropriate for manufacturing the microneedle patch (microneedle array) that is required to be manufactured with a low cost on a large scale.

The conventional methods have complicated steps of manufacturing the microneedle patch, and require large equipment to manufacture the microneedle patch having small surface roughness.

It is promising to manufacture the master plate for microneedle patch through exposure to a resist film as described above. Jpn. Pat. Appln. KOKAI Publication No. 2001-356187 discloses a XYθ stage apparatus used for the exposure apparatus, which precisely moves an object to be processed in a desired X-axis position, Y-axis position and θ-axis position at high speed. The XYθ stage apparatus includes a pair of linear motors disposed in an opposed relation to one another in the X-axis direction, a pair of linear motors disposed in an opposed relation to one another in the Y-axis direction perpendicular to the X-axis, a movable table on which the object to be processed is mounted, rotating support means for rotatably supporting the movable table in the θ-axis direction in the same plane as the X- and Y-axes, a XY encoder, a θ encoder, and a positional controller for controlling the X-axis position, Y-axis position and θ-axis position of the movable table by independently actuating the two pairs of liner motors.

However, it was difficult for the conventional exposure apparatus to expose the photoresist into a desired shape such as a cone. It was particularly difficult to manufacture a structure in which the same shapes are arrayed in parallel such as the microneedle array.

BRIEF SUMMARY OF THE INVENTION

It is an object of the invention to provide a method of manufacturing a master plate having various shapes, being formed into a deep position, and having a sharp tip and smooth surface by using a relatively simple process.

It is another object of the invention to provide a method of manufacturing a microneedle patch having plural microneedles with various shapes, and the microneedle patch.

It is still another object of the invention to provide an exposure apparatus capable of adjusting a relative angle of inclination between an exposing flux and a photoresist to enable exposure to be freely controlled.

A method of manufacturing a master plate of the invention comprises the steps of: forming a photoresist film on a substrate; disposing a photomask having a plurality of island radiation shields on the photoresist film followed by integrating the photomask and the photoresist film; applying light from a light source to the photoresist film through the photomask for selectively exposing the photoresist film; and developing the photoresist film to form a master plate, characterized in that the method includes irradiating the photoresist film with the light from plural directions through the photomask to selectively expose the photoresist film from the respective directions.

The photoresist may be selectively exposed by fixing the output direction of light from the light source, and by allowing the stage to be inclined in plural directions relative to the output direction of the light. This method contributes to simplifying the exposure apparatus.

The stage may be inclined in plural directions by allowing the stage to swing around a swing axis perpendicular to the irradiation direction of the light from the light source. This method permits the photoresist to be exposed from various directions.

The stage may be inclined in two symmetric directions relative to the irradiation direction of the light from the light source by allowing the stage to swing around a swing axis perpendicular to the irradiation direction of the light from the light source. This method contributes to simplifying the manufacturing process.

The stage may be inclined in plural directions by allowing the stage to swing around two or more swing axes perpendicular to the irradiation direction of the light from the light source. This method enables exposure from various directions.

The stage may be swung approximately along a circle arc centered at the swing axis. This method enables exposure from various directions.

The stage may be inclined in plural directions around a supporting point of a support of the stage. This method enables exposure from various directions.

The photoresist film may be selectively exposed by disposing the substrate, on which the photoresist film is formed with the photoresist disposed on the photoresist film, on the stage and by allowing the output direction of the light from the light source to change in plural directions. This method enables exposure from various directions.

The photoresist film may be selectively exposed by changing the output direction of the light from the light source in plural directions, and by allowing the stage to be inclined in two or more directions relative to the output direction of the light. This method enables exposure from further various directions.

The stage may be rotated. This method enables exposure from further various directions.

The photoresist film may be continuously irradiated with light while the stage is rotated. This method enables an unexposed portion of the photoresist film to be formed into a round cone.

The island radiation shield may be formed into a polygon, and the swing direction of the stage may be set in a direction connecting any one of the apexes and the center of the polygon, or in a direction perpendicular to any one of the sides of the polygon. This method makes setting of the swing direction easy.

The island radiation shield may be formed into a polygon, and the direction of inclination of the stage may be set in a direction connecting any one of the apexes and the center of the polygon, or in a direction perpendicular to any one of the sides of the polygon. This method makes setting of the inclination direction easy.

The island radiation shield may be formed into a polygon, and the stage may be rotated at an angle corresponding to any one of the interior angles of the polygon. This method makes setting of the angle of rotation easy.

The photoresist film may be a laminate of plural types of photoresist films having different refraction indices to one another. This method enables the unexposed portion of the photoresist film to be formed into a cone having discontinuously changing diameters.

The photoresist film may be exposed plural times at two or more wavelengths. This method also enables the unexposed portion of the photoresist film to be formed into a cone having discontinuously changing diameters.

A method of manufacturing a microneedle patch of the invention comprises the steps of: manufacturing a replication plate using a master plate having plural recesses or projections corresponding to the shape of the microneedle manufactured by the above method; and molding a microneedle patch having a plurality of microneedles using the replication plate.

An inversion plate having an inversed pattern of a master plate may be manufactured from the master plate by using a negative photoresist as the photoresist, and a replication plate having the inversed pattern may be manufactured from the inversion plate.

A positive photoresist may be used for the photoresist, and a replication plate having an inversed pattern of the master plate may be manufactured from the master plate.

The microneedle patch of the invention is manufactured using the above-mentioned method of manufacturing the microneedle patch, characterized in that the microneedles are disposed in parallel on a patch substrate.

The surface roughness of the microneedle is preferably 5 µm or less.

The shape of the microneedle may be a combination of a cone and a trapezoidal cone having discontinuously changing diameters.

The entire microneedles or a part of the microneedles are preferably made of a biocompatible material. Such a microneedle patch contributes to use in living bodies.

An exposure apparatus of the invention comprises: a stage on which a substrate is placed, the substrate having a photoresist film formed thereon and further having a photomask mounted thereon; a light output controller which controls output of light exited from a light source; a focus controller of the light; and a mechanism which adjusts a relative angle between an output direction of the light and the stage.

The mechanism which adjusts the relative angle between the irradiation direction of the light and the stage is, for example, a stage inclination mechanism which inclines the stage. The stage inclination mechanism is provided with, for example, a stage swing actuator or a stage inclination actuator. The stage swing actuator has, for example, a semi-cylindrical surface in contact with a guide at a lower face so that the stage swings along the guide, and a flat surface at the upper face. The stage inclination actuator causes, for example, a stage support which supports the stage to be inclined. Such an exposure apparatus facilitates adjustment of the angle of inclination of the stage relative to the irradiation direction of the light.

The stage may further include a stage rotation actuator which allows the stage to rotate. Such an exposure apparatus enables exposure from various directions.

The stage may further involve a stage translation actuator which allows the stage to perform translational movement. Such an exposure apparatus facilitates adjustment of the position of the substrate on the stage.

The stage may further include a light source translation actuator which allows the light source to perform translational movement. Such an exposure apparatus facilitates adjustment of the light irradiation position. The light may be uniformly irradiated on the photoresist film disposed on the stage when the surface area of the stage is large.

An irradiation direction controller which controls the irradiation direction of the light from the light source may be used as a mechanism which adjusts the relative angle between the irradiation direction of the light and the stage. Such an exposure apparatus facilitates adjustment of the light irradiation angle. The method of adjusting the irradiation direction of the light includes changing the angle and refraction of a lens system or a mirror system where light passes.

The light may be continuously applied to the photoresist film while the stage is rotated with the stage rotation actuator. Such an exposure apparatus enables the unexposed portion of the photoresist film to be formed into a cone.

The light may be irradiated plural times at varied light wavelengths with a light output controller. Such an exposure apparatus enables the unexposed portion of the photoresist film to be formed into a cone having discontinuously changing diameters.

According to the method of manufacturing the master plate of the invention, the master plate for manufacturing a fine structure of various conical shapes may be prepared by applying light to the photoresist film from various directions. Since the master plate has low surface roughness with a smooth surface, peelability in peeling the structure from the master plate is excellent, and defects such as breakage of the needle upon peeling may be suppressed, which contributes to improving productivity. The microneedle obtained by the invention has a good feeling of use since the surface is smooth.

The exposure apparatus of the invention can adjust the relative directional relation between the irradiation direction of the light and the photoresist film, making it possible to freely control the unexposed portion of the photoresist film.

BRIEF DESCRIPTION OF THE SEVERAL VIEWS OF THE DRAWING

FIGS. 6A to 6D show plane views of examples of the island radiation shields.

FIG. 10 shows a perspective view of an inverse plate.

FIG. 11 shows a flow chart illustrating a process for manufacturing a microneedle patch from the master plate.

FIG. 13 shows a perspective view of the microneedle patch.

FIG. 16 shows a perspective view of the mechanism in FIG. 15 disposed on a stage translation actuator and a stage rotation actuator.

FIG. 17 shows a perspective view of an exposure apparatus provided with a stage swing actuator, a stage inclination actuator and a stage support.

FIG. 18 shows a perspective view illustrating the main part of an exposure apparatus provided with an irradiation direction controller.

DETAILED DESCRIPTION OF THE INVENTION

Embodiments of the invention will be described below. Photoresists and chemicals necessary for manufacturing the master plate are not limited to those shown in the examples, and corresponding ones known in the art may be appropriately used.

Figure 1:
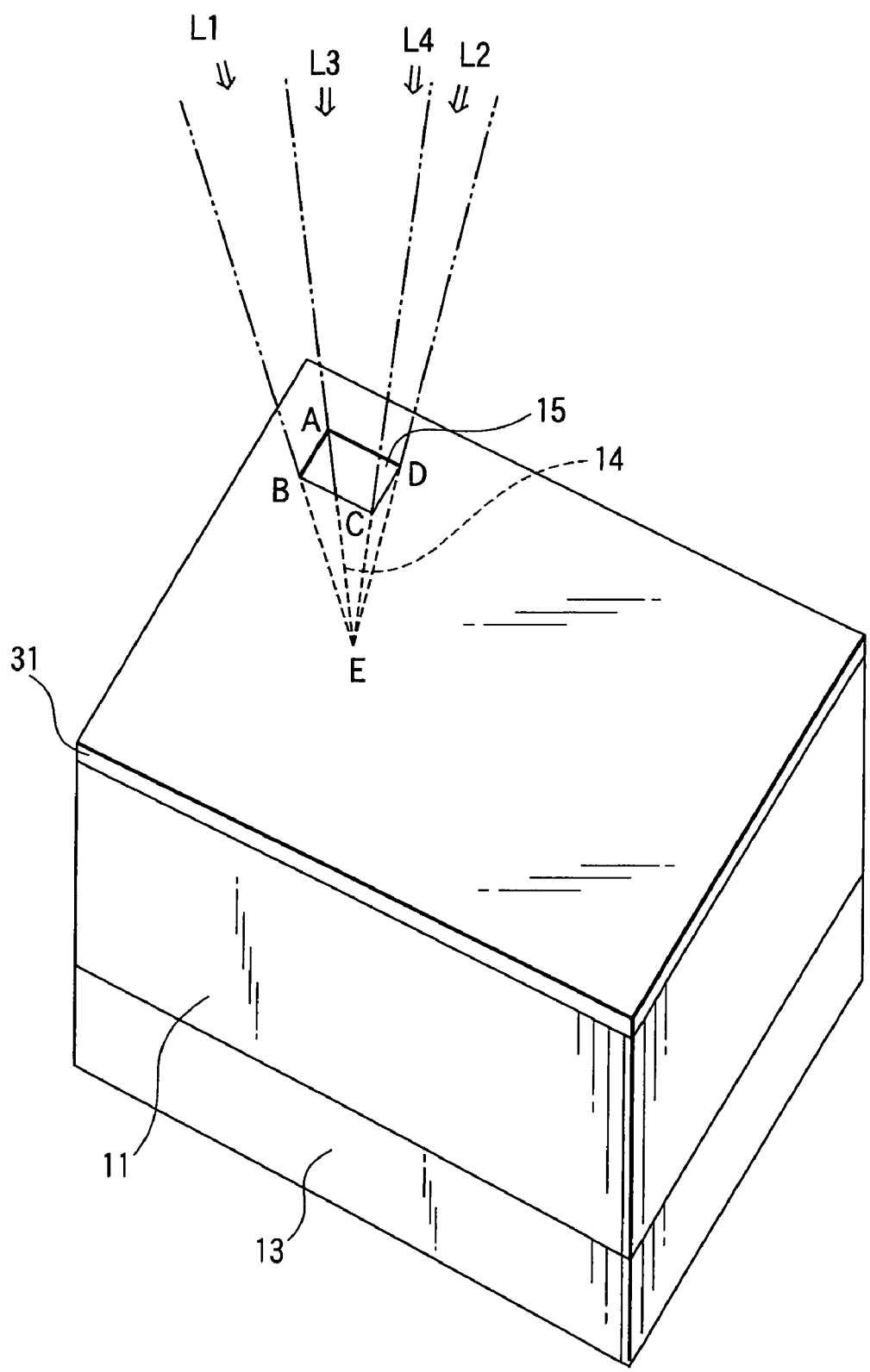
FIG. 1 shows a perspective view illustrating an aspect for forming a conical unexposed portion by irradiating a photoresist film with light.

FIG. 1 is a perspective view illustrating an aspect for forming a conical unexposed portion 14 by irradiating a photoresist film 11 with light.

First, the photoresist film 11 is formed on a substrate 13. A photomask 31 having island radiation shields 15 are disposed on the photoresist film 11, and the photomask and the photoresist film are integrated. Integrating the photoresist film 11 and photomask 31 eliminates alignment of the photomask when the light is applied to the photoresist film 11 from plural directions as described below, and there arises no problem of alignment deviation. Then, a part of the photoresist film 11 is selectively exposed by irradiating the photoresist film 11 with light, for example UV light, from a light source through the photomask 31. The photomask 31 is removed thereafter from the photoresist film 11, and the photoresist film is developed.

Silicon (Si), glass, ceramic, quartz, sapphire or the like may be used as the substrate 13.

Examples of the photoresist film 11 available include those prepared from a material such as Nano SU-8 (trade name, manufactured by Microchem Co., Ltd., epoxy-based) and TMMRS 2000/TMMFTS 2000 (trade names, manufactured by Tokyo Ohka Kogyo Co., Ltd.). A thick film may be formed by using such a photoresist film 11.

A spin coater may be used for applying the photoresist film 11 to the surface of the substrate 13. The spin coater is an apparatus for forming a uniform photoresist film by dripping a photoresist solution on the surface of the substrate while the substrate is rotated at a high speed (for example at 1000 rpm for 30 seconds) after fixing the substrate on a rotation support.

Alternatively, the photoresist film 11 may be deposited by spraying the photoresist solution onto the substrate 13 using a spray jet.

The photoresist film 11 is classified into a negative type and a positive type. While the unexposed portion of the negative photoresist film is dissolved in organic solvents, the exposed portion thereof becomes insoluble in the solvent by a photochemical reaction. Accordingly, the exposed portion remains as a resist pattern after development.

On the other hand, the exposed portion of the positive photoresist becomes soluble in an alkaline developer by the photochemical reaction.

Since the negative photoresist has good adhesiveness with the wafer, it is used for wet etching with a chemical. On the other hand, since the positive photoresist is high in resolution, it is used for dry etching by plasma.

Many island radiation shields 15 made of Cr or the like are provided on the photomask 31. The photomask 31 is closely adhered to the photoresist film 11 to laminate the latter on the former, and they are integrated with one another. The material used for the island radiation shield 15 of the photomask 31 depends on the wavelength of the light (L1 to L4) from the light source. For example, Pb is preferable when X-ray is used.

When the negative photoresist is used and the light is applied to the photoresist film 11 through the photomask 31, the unexposed portion 14 where the light is blocked with the island radiation shield 15 is not hardened, while the exposed portion not blocked with the island radiation shield 15 is hardened.

A master plate for manufacturing the microneedle patch may be prepared in the invention by, for example, forming a conical unexposed portion 14 having the same rectangular bottom face as the island radiation shield 15 as shown in FIG. 1, and by removing the unexposed portion 14 through development as will be described below.

When the positive photoresist is used, the photomask 31 may be used as a substrate without using the substrate 13. Since the conical unexposed portion under the photomask 31 is insoluble in the alkaline developer when the positive photoresist is used, the unexposed portion is left behind after development. Since a cone corresponding to the microneedle to be formed is formed under the photomask 31 as described above, the photomask 31 may be used as the substrate.

The method of forming the above-mentioned cone in the invention will be described below.

In principle, the light is applied to the photoresist film from two or more directions through the photomask 31 in this invention. As shown in FIG. 1, light beams (L1, L2, L3, L4) are applied relatively inclined to the photoresist film 11, and an unexposed portion 14 having a square cone shape (ABCD-E) is formed.

The light beam (L1) is applied parallel to the side face ABE, the light beam (L2) is applied parallel to the side face CDE, the light beam (L3) is applied parallel to the side face BCE, and the light beam (L4) is applied parallel to the side face ADE in order to determine the position of the apex E. In other words, the surface of the photomask 31 is exposed plural times (four times in the case of FIG. 1) in which the irradiation direction is different for each light beam L (L1 to L4).

The unexposed portion 14 blocked with the island radiation shield 15 may be formed into a desired cone shape by plural times of exposure. The frequency of exposure and direction of exposure depend on the shape of the island radiation shield 15, the shape of the desired cone, and the axis of symmetry of a symmetrical shape.

The invention proposes three methods for irradiating the light from plural directions, i.e., a method of displacing the stage that supports the substrate, a method of changing the output direction of the light from the light source, and a method of combining the both methods.

Figure 2A:
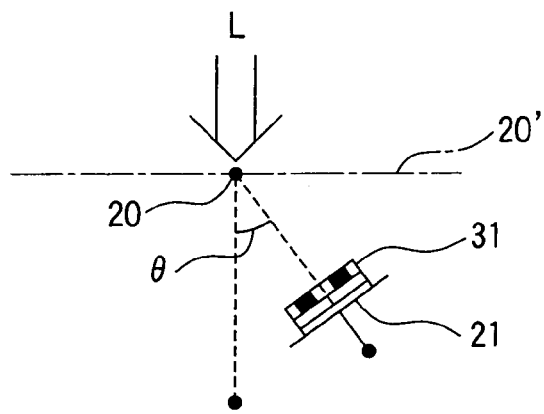
FIGS. 2A to 2C show schematic views illustrating a method of displacing a stage which supports a substrate.
Figure 2B:
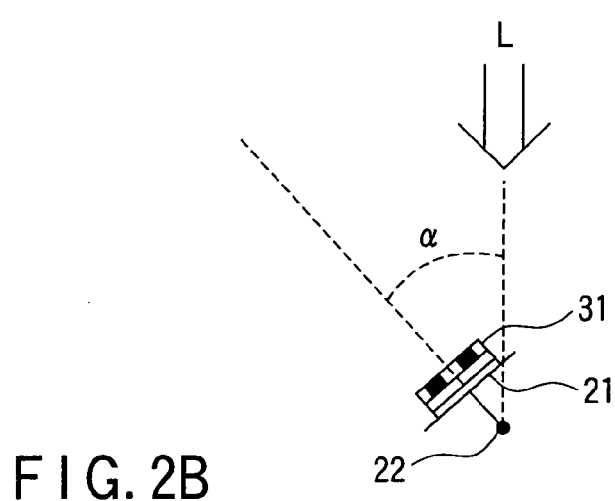
Figure 2C:
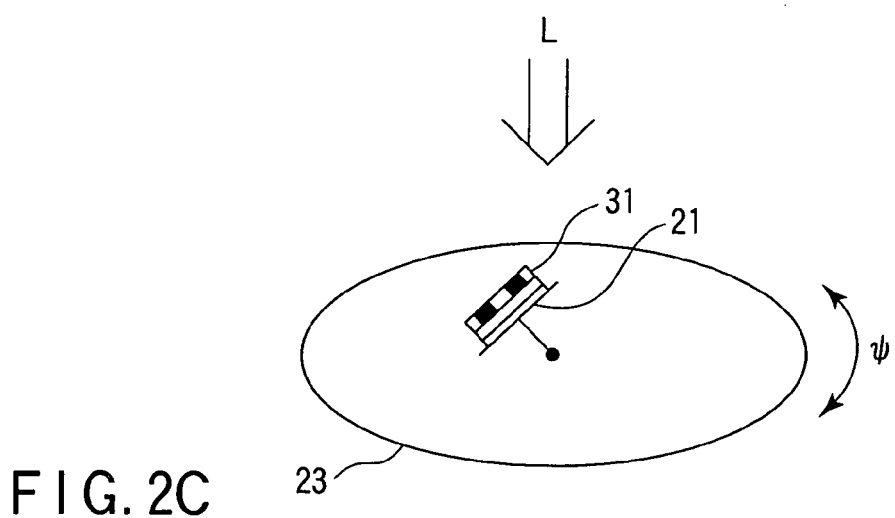

FIGS. 2A to 2C show schematic views illustrating the method of displacing the stage that supports the substrate.

The output direction of the light L from the light source is vertically and downwardly fixed in FIG. 2A. On the other hand, a photoresist-coated substrate on which the photomask 31 is mounted is placed on a stage 21, and the stage 21 is inclined at an angle θ from the center line as an imaginary swing axis 20 in the right direction as shown in the drawing, and the light from the light source is applied to the photoresist film through the photomask 31.

Subsequently, the light is applied while the stage 21 is symmetrically inclined (in the left direction in the drawing) at an angle θ from the swing axis 20 as a center relative to the light L from the light source. Consequently, two times of symmetrical exposure is possible in inclined directions such as L1 and L2 in FIG. 1.

While a symmetrical cone may be formed by applying the light at approximately symmetrically inclined two angles relative to the output direction of the light in the example of the invention, the angle of inclination may be arbitrarily determined depending on the desired shapes.

Further, a swing axis 20' perpendicular to the swing axis 20 is provided, and the stage 21 may be inclined relative to the swing axis 20' as a center line. In this case, the stage 21 may be swung in a direction perpendicular to the surface of the drawing in addition to the right and left direction in the drawing. This allows the light beam L to irradiate the stage from four directions of L1 and L2 directions as well as L3 and L4 directions.

For allowing the stage 21 to swing as described above, regulation means for regulating the direction of swing along an approximately circular arc around the swing axis 20, for example a guide, is used.

The output direction of the light beam L from the light source is fixed to a downwardly vertical direction in FIG. 2B. In FIG. 2B, the stage 21 is inclined at an angle α in left direction in the drawing from a supporting point 22 of the stage support as a center, and the light from the light source is applied to the photoresist film through the photomask 31.

Subsequently, the stage 21 is symmetrically inclined at an angle α (in the right direction in the drawing) relative to the light beam L from the light source around the supporting point 22 as a center to perform light irradiation. These operations allow the same effect as in FIG. 2A to be obtained. The stage may be also configured to be inclined perpendicularly to the surface of the drawing.

A mechanism such as a tripod head may be used, for example, as the supporting point 22 shown in FIG. 2B.

In FIG. 2C, the stage 21 is mounted on a rotating table 23 with a given angle of inclination, and is rotated at an angle φ together with the rotating table 23. The irradiation direction of the light to the photoresist film 11 on the stage 21 changes depending on the angle of rotation φ in this configuration. For example, the photoresist film 11 may be irradiated with the light from four directions of L1 to L4 as shown in FIG. 1 by allowing the stage to rotate by 90° from the state shown in the drawing.

It is an advantage of this method that the light may be irradiated from plural directions only by allowing the stage 21 to rotate with the rotating table 23 by placing the stage 21 aslant on the rotating table 23.

The output direction of the light L from the light source may be changed in place of displacing the stage 21 as shown in FIGS. 2A to 2C. The output direction of the light may be changed in four directions for obtaining the same effect as in FIG. 1 using this method. An optical system for enabling the light to be exited in different directions may be provided at the light source so that the output direction can be promptly and simply changed.

The angle of rotation of the stage or the range of variation of the output angle of the light from the light source may be reduced by changing the output direction of the light from the light source in combination with rotation of the stage 21.

Figures 3A, 3B:
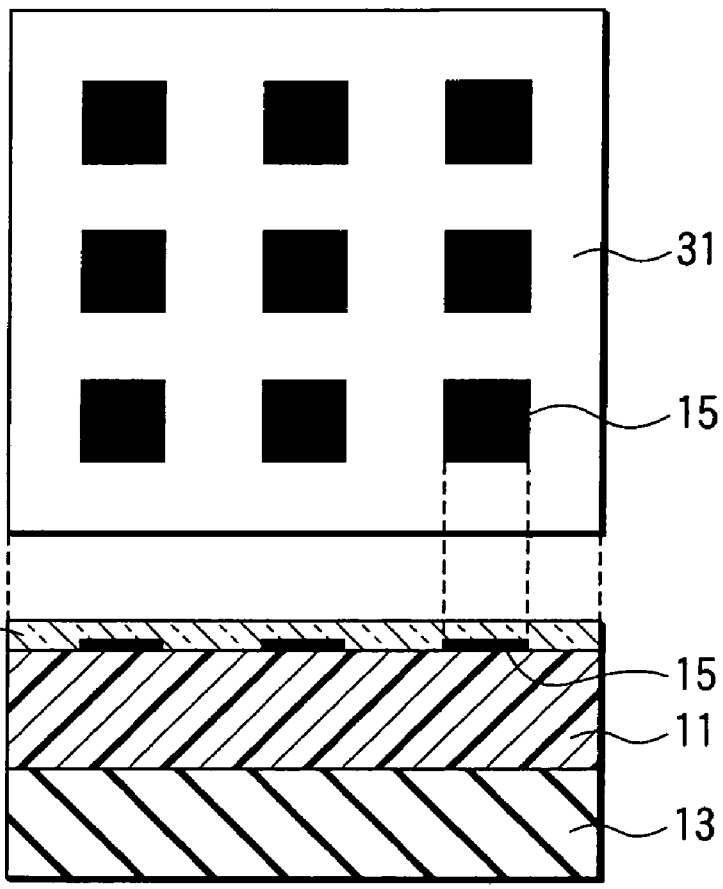
FIGS. 3A and 3B show a plane view and cross-sectional view of an aspect in which a photomask is closely adhered to the photoresist film.

FIGS. 3A and 3B are a plane view and cross-sectional view illustrating the photomask 31 closely adhered to the photoresist 11. As show in FIG. 3A, square island radiation shields 15 are provided on the photomask 31. A master plate having nine fine square cones may be manufactured by using the photomask 31.

As shown in FIG. 3B, the photoresist film 11 is coated on the substrate 13, and the photomask 31 is closely adhered to the photoresist film 11. The size and shape of the island radiation shield 15 are determined depending on a desired three-dimensional shape and the angle of the irradiation light.

FIGS. 4A to 4E are cross-sectional views illustrating the process for forming conical unexposed portions using the negative photoresist film 11.

Figure 4A:
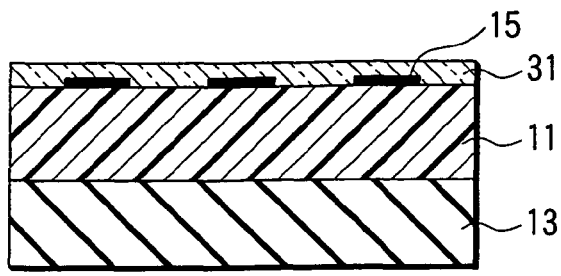
FIGS. 4A to 4E show cross-sectional views illustrating a process for forming the conical unexposed portion.

FIG. 4A shows the state that the photoresist film 11 is applied on the substrate 13, the photomask 31 on which the island radiation shields 15 are disposed is closely adhered to the photoresist film, and the photomask is integrated with the photoresist film so that the island radiation shields are horizontally disposed.

Figure 4B:
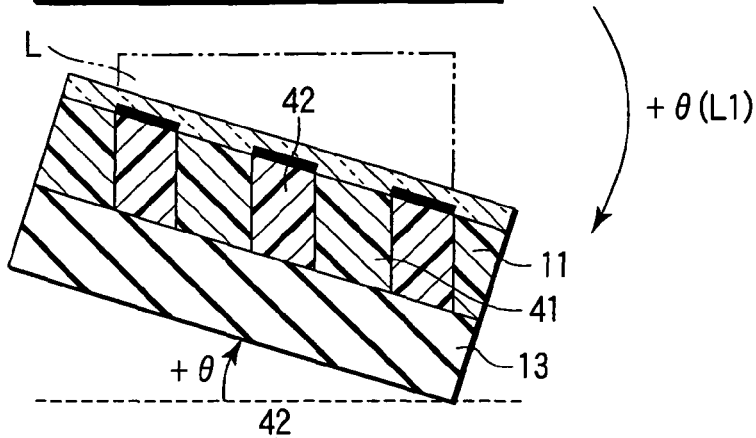

As shown in FIG. 4B, the light (L1) is applied in the state that the stage is inclined at an angle of +e by swinging the stage (not shown) on which the substrate is mounted. An exposed portion 41 is formed by allowing the light L1 to arrive at a part below the island radiation shield 15.

Figure 4C:
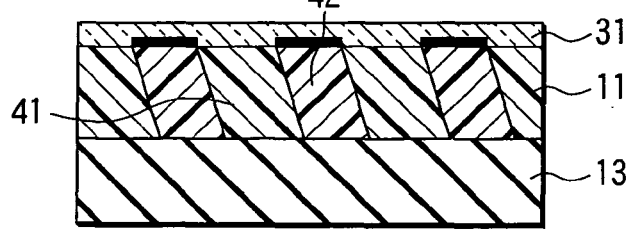

FIG. 4C shows the exposed portion 41 and unexposed portion 42 when the substrate 13 resumes horizontal from the state shown in FIG. 4B.

Figure 4D:
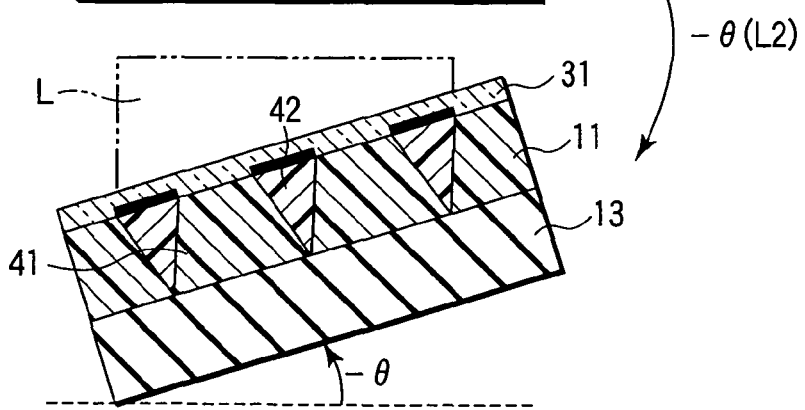
Figure 4E:
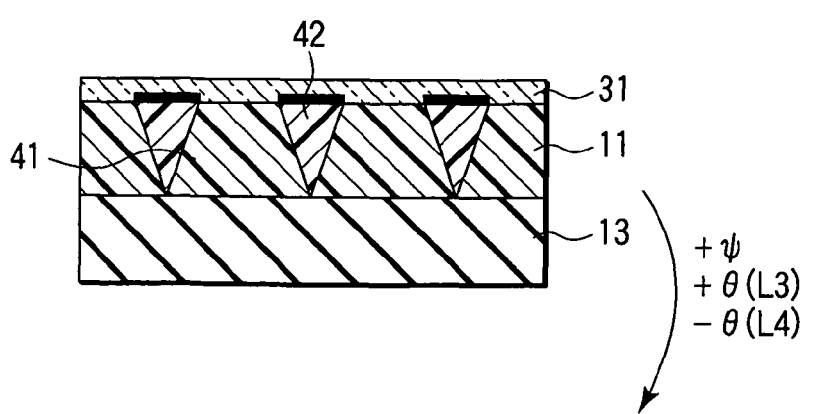

Subsequently, the stage is inclined at an angle −θ in an inverse direction as shown in FIG. 4D, and the irradiation of the light (L2) is performed. As a result, a triangular column of the unexposed portion 42 is formed below the island radiation shield as shown in FIG. 4E.

The stage is rotated at an angle +φ thereafter. Since the island radiation shield is a square in the drawing, angle of rotation φ of the stage is set to 90°. The stage is swung as described above, and the light (L3) is applied at an angle of inclination 9 and the light (L4) is applied at an angle of inclination −θ.

An unexposed portion in the shape of a square cone (ABCD-E) as shown in FIG. 1 is formed by four times of exposure (L1, L2, L3, L4).

Application of light from various directions is possible by inserting a step for rotating the stage between the steps for applying the light while the stage is swung. In this case, the light is applied at approximately symmetrical two positions with respect to the output direction of the light from the light source. This means that a step for applying the light at an angle of inclination of +θ of the stage is effectively combined with a step for applying the light at an angle of inclination of −θ of the stage.

The same effect may be obtained by allowing the stage 21 itself to incline, in place of allowing the stage 21 to swing. Accordingly, swing (θ) of the stage is substantially equivalent to inclination (α) of the stage, and these two methods are appropriately compatible.

The light is not always applied to a stationary photoresist film 11. The light may be continuously applied to the photoresist film 11 on the stage 21 while the stage 21 is rotated. This method allows a conical unexposed portion 14 having a curved line at the bottom such as a round cone to be readily formed.

FIGS. 5 and 6 are plane views illustrating examples of the island radiation shields 15. The shape of the island radiation shields 15 is the same as the shape of the bottom face of the conical unexposed portion 14. The shape of the side face of the cone depends on the irradiation direction of the light.

Figure 5A:
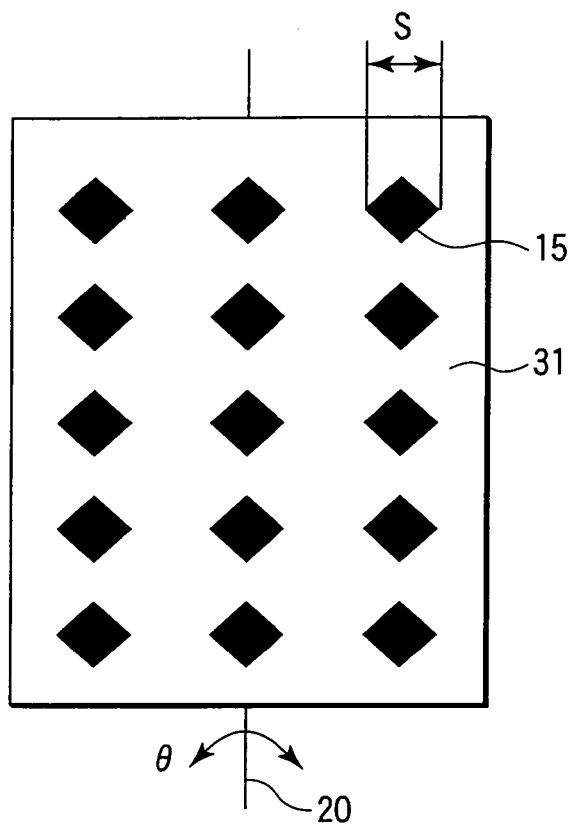
FIGS. 5A and 5B show plane views of examples of island radiation shields.
Figure 5B:
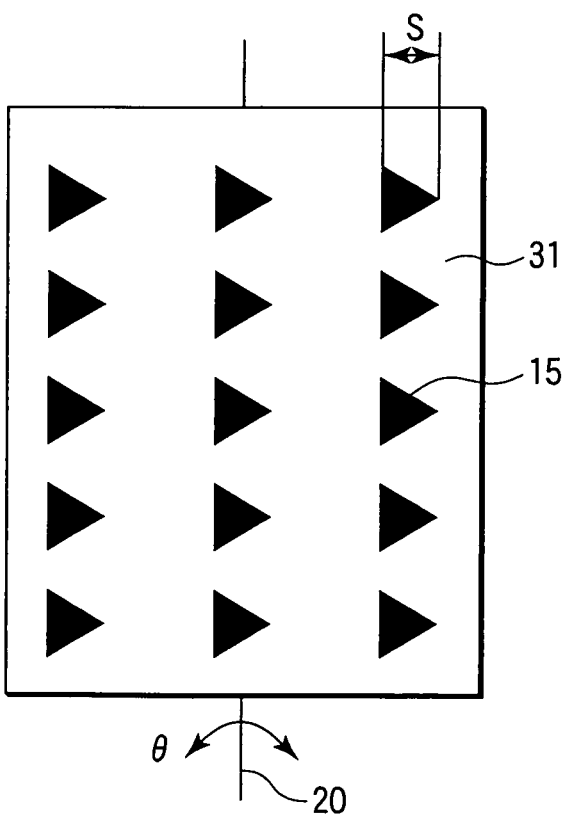

For example, when a square island radiation shield 15 with a size (S) of a diagonal line of, for example, 88 μm as shown in FIG. 5A is used and the swing angle θ is set to ±10°, a square cone with a height of 250 μm is obtained by giving rotation once. When a triangular island radiation shield 15 with a size (S) of the height as shown in FIG. 5B is used and the swing angle θ is set to ±10°, a triangular cone may be obtained by giving rotation twice.

FIGS. 6A to 6D show polygons used for the island radiation shields 15. An unexposed portion of the regular polygonal cone may be formed by setting the swing direction of the stage in a direction connecting any one of apexes and the center of the polygon, or in a direction perpendicular to any one of the sides of the polygon. The angle of rotation of the stage may be set to any one of interior angles of the polygon.

FIG. 6A is an example where the island radiation shield 15 is a regular octagon, and the number of the swing axes is four. The swing axis extends in a direction that connects an apex and the center of the octagon. FIG. 6B is an example where the island radiation shield 15 is a regular octagon, and the number of the swing axes is four. The swing axis is extended in a direction perpendicular to each side of the regular octagon. FIG. 6C is an example where the island radiation shield 15 is a regular hexagon, and the number of the swing axes is three. FIG. 6D is an example where the island radiation shield 15 is approximately a circle, and the number of the swing axes is eight.

Figure 7A:
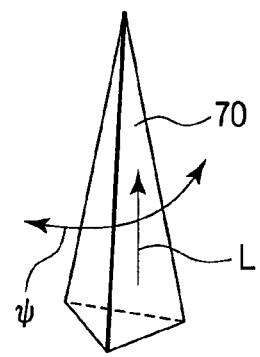
FIGS. 7A to 7D show perspective views illustrating conical unexposed portions.
Figure 7B:
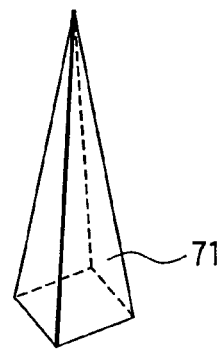
Figure 7C:
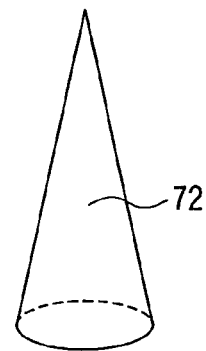
Figure 7D:
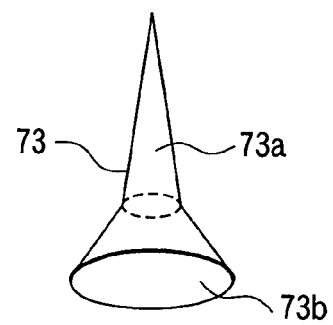

FIGS. 7A to 7D show perspective views illustrating cones of unexposed portions. When the island radiation shield 15 is a polygon as described above, a pyramidal unexposed portion 70 or 71 may be formed as shown in FIGS. 7A and 7B. When the island radiation shield 15 is a polygon having many apexes or a circle, an unexposed portion 72 close to a circular cone may be formed as shown in FIG. 7C. An unexposed portion 73 configured as a cone having indefinite angles of inclination of the side wall may be obtained as follows as shown in FIG. 7D.

Figure 8A:
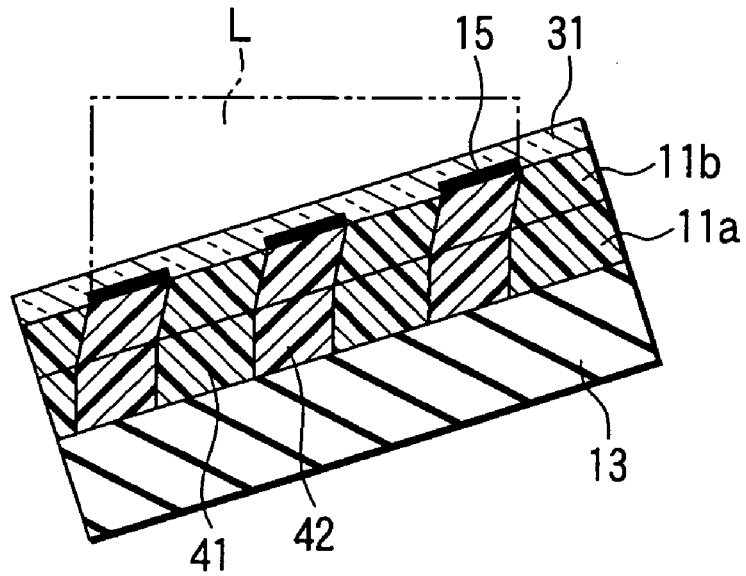
FIGS. 8A to 8C show a process for forming a conical master plate having varying diameters using a negative photoresist.
Figure 8B:
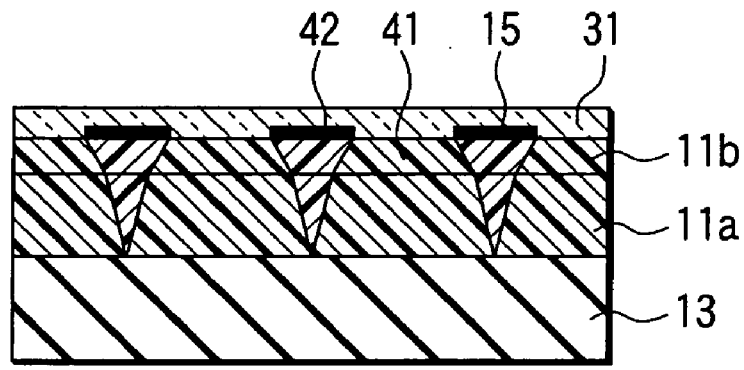
Figure 8C:
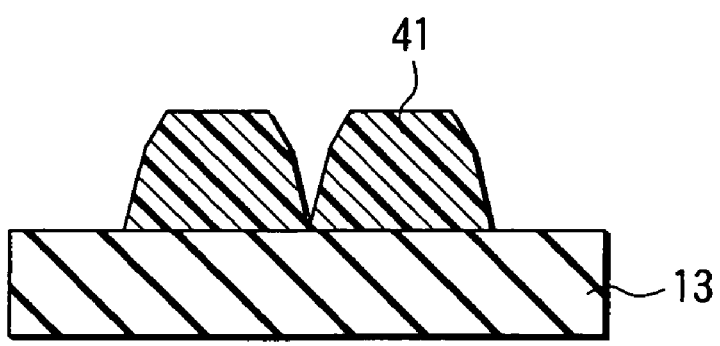

FIGS. 8A to 8C show cross-sectional views illustrating the method of forming the unexposed portion configured as a cone having indefinite angles of inclination of the side wall shown in FIG. 7D.

As shown in FIG. 8A, plural photoresist films 11a and 11b having different refractive indices to one another are laminated on a substrate 13. In this example, a resist (Nano SU-8, manufactured by Microchem Co., Ltd., an epoxy-based resin) having a high refractive index of 1.63 is used as the lower photoresist film 11a with a thickness of 300 μm, and a resist (ZED-400, manufactured by Zeon Corporation, a polycarbonate-based dry film) having a low refractive index of 1.59 is used as the upper photoresist film 11b. The irradiated light is refracted at the boundary between the two layers of the photoresist films 11a and 11b due to the difference in refractive indices.

When light beams are applied from plural directions, an unexposed portion 42 configured as a cone having discontinuously changing diameters at the boundary between the two layers of the photoresist films 11a and 11b is formed as shown in FIG. 8B.

Upon subsequent development, a master plate having recesses with a large diameter at the upper portion and sharp tip at the lower portion are formed where the unexposed portions 42 are removed as shown in FIG. 8C.

The strength of the microneedle manufactured by using such a master plate is reinforced at the bottom since a trapezoidal cone having a large diameter is formed at the base of a sharp cone.

It should be noted that even when one type of a photoresist film is used and the light is applied plural times with changing wavelengths of the irradiation light, an unexposed portion configured as a cone having indefinite angles of inclination of the side wall may be formed under the island radiation shield 15 as in FIG. 8B.

FIGS. 9A to 9F show cross-sectional views illustrating the process for forming a replication plate from a master plate.

Figure 9A:
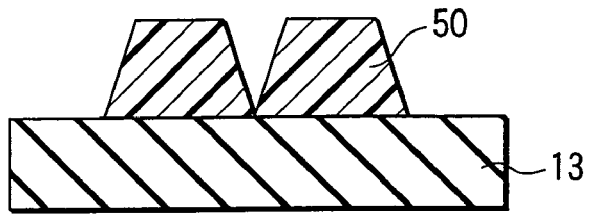
FIGS. 9A to 9F show cross-sectional views illustrating a process for forming a replication plate from the master plate.

When the photomask 31 is removed from the photoresist film on which cones of the unexposed portions 42 are formed and development is performed, a resist pattern 50 having recesses corresponding to the microneedles is formed on the substrate 13 as shown in FIG. 9A.

Figure 9B:
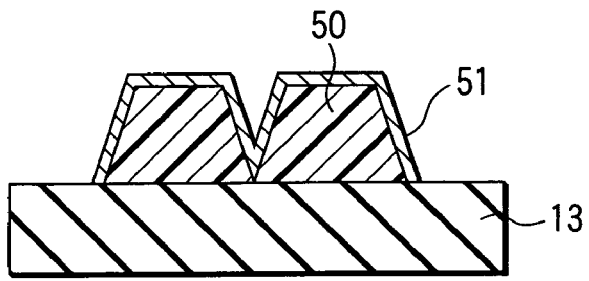

A thin metal layer is coated on the surface of the resist pattern 50 as shown in FIG. 9B by electroless plating or sputtering to form a conductive layer 51.

Figure 9C:
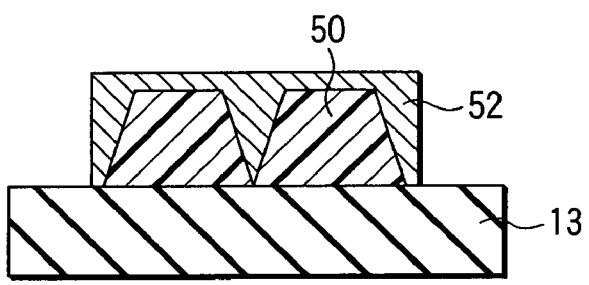

Subsequently, a plating layer 52 is formed by electroplating or electroforming as shown in FIG. 9C.

Figure 9D:

An inversion plate 60 as an inversion pattern of the master plate is obtained by peeling the plating layer 52 as shown in FIG. 9D.

FIG. 10 shows a perspective view of the inversion plate 60. As shown in FIG. 10, the inversion plate 60 is a relief duplicator having projected molding portions 70 configured as cones.

Figure 9E:

As shown in FIG. 9E, a plating layer 80 is formed by electroforming on the inversion plate 60.

Figure 9F:
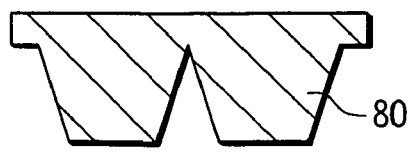

As shown in FIG. 9F, a replication plate 80 as an inversion pattern of the inversion plate is obtained by peeling the plating layer 80.

Metals such as Ni, Cr, Cu and Zn may be used for plating materials or electroforming materials for forming the inversion plate 60 and replication plate 80. Resin materials and ceramic materials are also available.

FIG. 11 is a flow chart illustrating the process for manufacturing the microneedle patch from the master plate.

A master plate corresponding to the shape of the microneedle patch is manufactured at first (S1).

Then, an inversion plate having an inversion pattern of the master plate is manufactured, and a replication plate as an inversion of the inversion pattern is manufactured (S2).

A sheet as a material of the microneedle patch is placed on the replication plate followed by pressurizing with heating, and the pattern of the replication plate is transcribed onto the sheet for shaping (S3).

The sheet is peeled from the replication plate after allowing heat to be dissipated, and is cut into a shape of a patch (S4).

Finally, the patch is inspected (S5) to obtain a microneedle patch.

A chitin/chitosan sheet is used when the microneedle patch is manufactured from chitin/chitosan. The chitin/chitosan sheet is manufactured as follows. After dissolving chitin in a MeOH solution of Ca, chitin is precipitated by adding a large volume of water. A white gel containing 4 to 5% of chitin is obtained by removing Ca by dialysis. The gel is dispersed in distilled water, the solution is formed into a sheet by processing with a papermaking machine, and a sheet containing 100% of chitin is manufactured after press-drying the sheet.

While a negative photoresist has been used in the above-mentioned examples, a positive photoresist may also be used.

FIGS. 12A to 12D show cross-sectional views of a process for forming a master plate using a positive photoresist. As shown in FIGS. 12A to 12D, a photomask 31 disposed on the photoresist 90 serves as a substrate when the positive photoresist 90 is used.

Figure 12A:
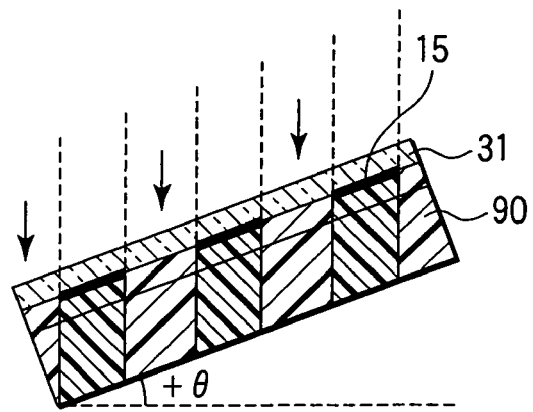
FIGS. 12A to 12D show cross-sectional views illustrating a process for forming a master plate using a positive photoresist.

The photoresist 90 is inclined at an angle $+\theta$ as shown in FIG. 12A, and light is vertically applied downward through the photomask 31. An exposed portion (alkali-soluble) 91 not shielded with an island radiation shield 15 and an unexposed portion (alkali-insoluble) 92 shielded with the island radiation shield 15 are formed on the photoresist 90.

Figure 12B:
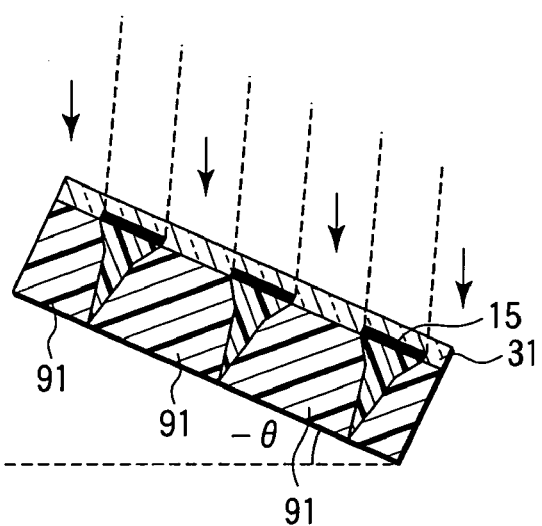
Figure 12C:
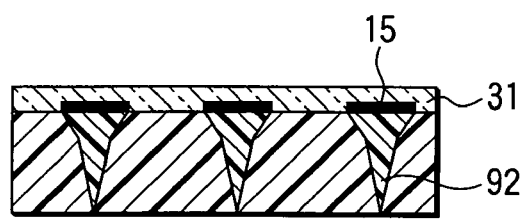

Then, the photoresist 90 is inclined at an angle $-\theta$ as shown in FIG. 12B, and light is vertically applied downward through the photomask 31. Consequently, the exposed portion (alkali-soluble) 91 and unexposed portion (alkali-insoluble) 92 of the photoresist 90 are formed in the shapes as shown in FIG. 12C.

Figure 12D:
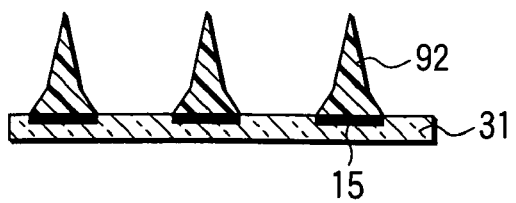

By performing development with an alkali developer without removing the photomask 31, a master plate having recesses with a shape corresponding to a desired microneedle is provided on the photomask 31 as shown in FIG. 12D.

A replication plate may be directly manufactured without intervention of an inverse plate by plating the master plate followed by peeling the plating layer.

FIG. 13 shows a perspective view of a microneedle patch 101. One microneedle 70 corresponds to one island radiation shield, and many microneedles 70 having an approximately the same shape are disposed on a patch substrate 100 depending on the arrangement of the island radiation shields.

The exposure apparatus of the invention will be described below.

Figure 14:
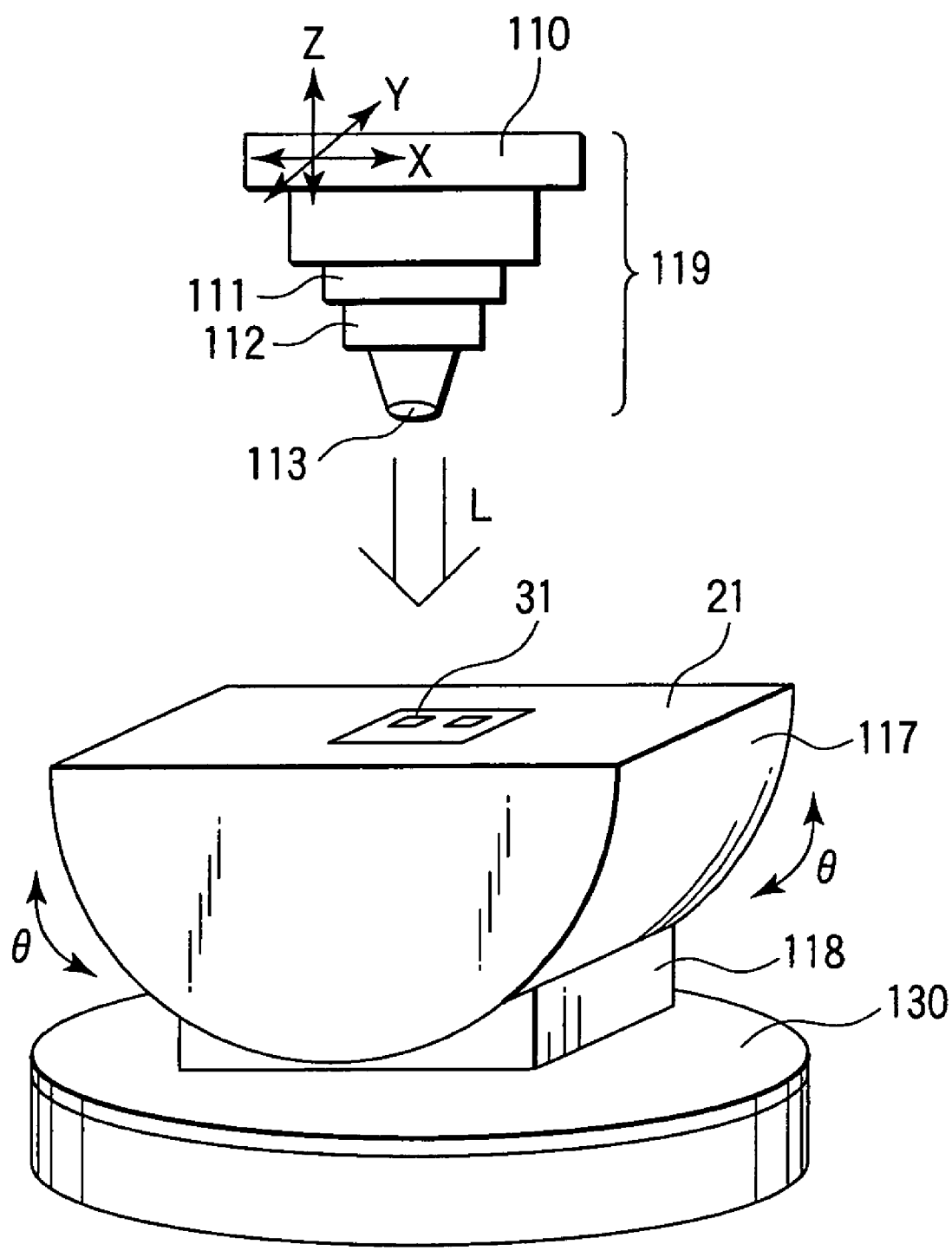
FIG. 14 shows a perspective view illustrating the main part of an exposure apparatus having a stage swing actuator.

FIG. 14 is a perspective view illustrating the main part of an exposure apparatus having a stage swing actuator. This exposure apparatus is used for implementing the exposure method shown in FIG. 2A.

An exposure optical system 119 of the exposure apparatus shown in FIG. 14 includes a light source translation actuator 110, a light output controller 111, a focus controller 112 and an output port 113. The light source translation actuator 110 has an arm mechanism, and enables translational movement of the exposure optical system 119 in three-dimensional directions.

A stage rotation actuator 130 is provided below the exposure optical system 119. The stage rotation actuator 130 includes thereon a guide 118 and a semi-cylindrical swing actuator 117 swingably supported on the guide 118. The bottom face of the swing actuator 117 is a half-cylinder in contact with the guide 118. The swing actuator 117 is provided with a driving system and a control system for allowing the swing actuator to swing relative to the guide 118. A flat stage 21 is provided on the upper face of the swing actuator 117, and a photoresist-coated substrate having the photomasks 31 mounted thereon is placed on the stage 21 so as to face the exposure optical system 119.

The exposure method using the exposure apparatus will be described below. A photoresist-coated substrate on which the photomask 31 is mounted is placed on the stage 21. The output direction of the light L from the output port 113 is vertically fixed downward. The stage 21 is inclined at an angle $\theta$ in one direction by means of the swing actuator 117, and the light from the light source is applied to the photoresist film through the photomask 31. Then, the stage 21 is inclined at an angle $\theta$ in a reverse direction by means of the swing actuator 117, and the light from the light source is applied to the photoresist film through the photomask 31. Subsequently, the guide 118 and swing actuator 117 are rotated, for example, at an angle 90° by means of the stage rotation actuator 130 while the stage 21 remains fixed. The photoresist is exposed thereafter by inclining the stage 21 at an angle θ in one direction, followed by exposing the photoresist by inclining the stage 21 at an angle θ in a reverse direction. Consequently, irradiation of the light L can be performed from four directions as shown in FIG. 1.

Figure 15:
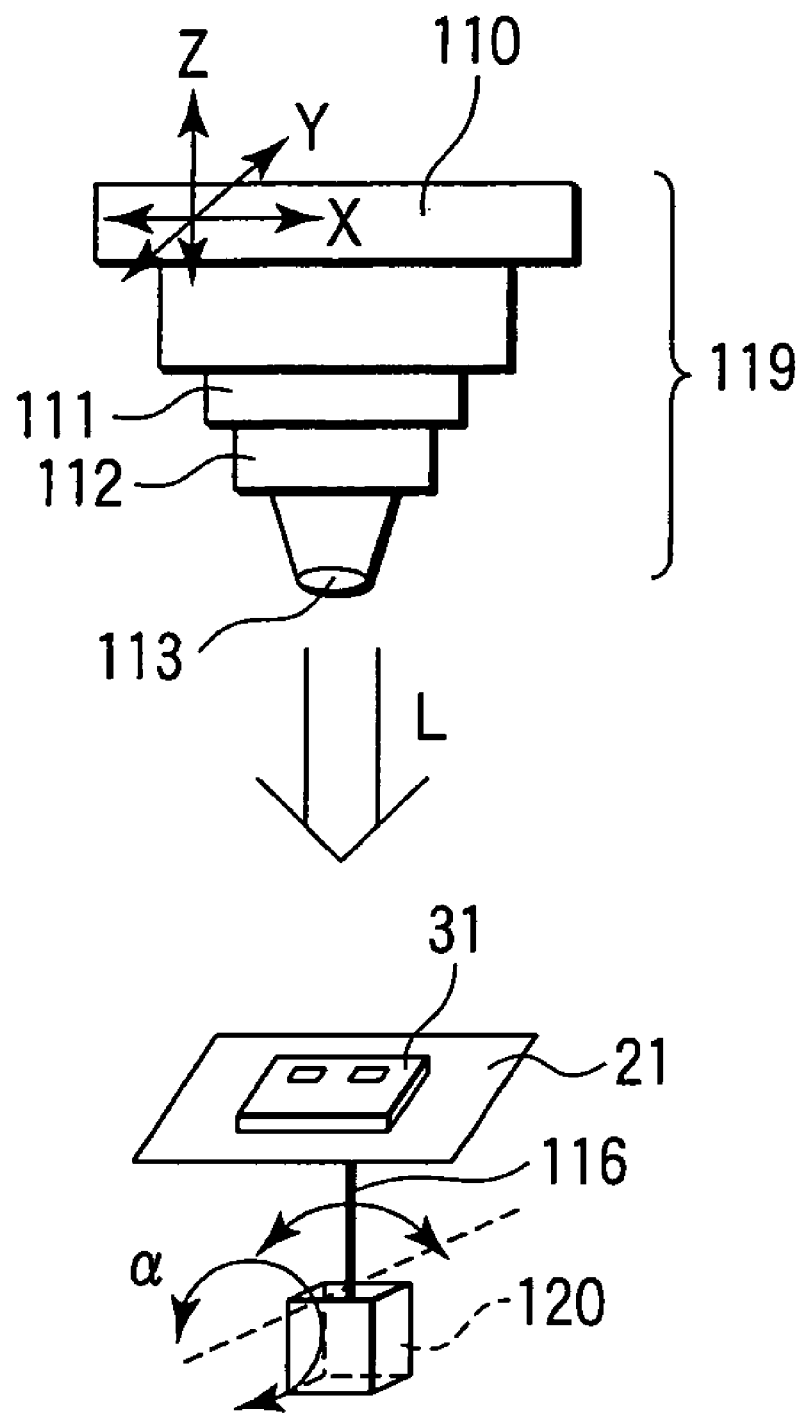
FIG. 15 shows a perspective view illustrating the main part of an exposure apparatus having a stage inclination actuator.

FIG. 15 is a perspective view illustrating a main part of the exposure apparatus having a stage inclination actuator. This exposure apparatus is used for implementing the exposure method shown in FIG. 2B.

A stage inclination actuator 120 is provided below the exposure optical system 119. A stage support 116 is attached to the stage inclination actuator 120, and the stage support 116 is configured to be inclined around a supporting point as a center. The stage inclination actuator 120 has a driving system and a control system for allowing the stage support 116 to be inclined at a given angle. The connection part between the stage support 116 and the stage inclination actuator 120 is configured as a tripod head for a camera. A gear mechanism may be provided at the stage support 116 or stage inclination adjustment means 120 at the junction between the stage support 116 and the stage inclination actuator 120. The stage 21 is supported on the stage support 116. The photoresist-coated substrate on which the photomask 31 is mounted is placed on the stage 21 with interposition of, for example, a chuck so as to face the exposure optical system 119.

FIG. 16 is a perspective view of the mechanism shown in FIG. 15 disposed on the stage translation actuator and the stage rotation actuator.

As shown in FIG. 16, a stage translation actuator 131 is provided below the exposure optical system 119, and the stage rotation actuator 130 is provided on the stage translation actuator 131. The stage inclination actuator (not shown), the stage support 116 and the stage 21 in FIG. 15 are provided on the stage rotation actuator 130.

The stage translation actuator 131 enables three-dimensional translational movement, and various mechanisms may be appropriately used. The stage rotation actuator 130 rotates the stage 21 at a given angle with interposition of the stage inclination actuator and the stage support 116. The stage rotation actuator 130 has a driving system and a control system for rotating the stage with a given control signal.

Any one of the stage translation actuator 131 and the stage rotation actuator 130, or both of them, may be provided in the exposure apparatus of the invention.

While the stage swing actuator 117 is used in FIG. 14, and the stage inclination actuator 120 and the stage support 116 are used in FIG. 15, as means for inclining the stage 21, both of the means may be used.

FIG. 17 is a perspective view of an exposure apparatus provided with the stage swing actuator 117, the stage inclination actuator (not shown) and the stage support 116.

FIG. 18 is a perspective view illustrating a main part of an exposure apparatus provided with an irradiation direction controller.

The exposure optical system 119 of the exposure apparatus in FIG. 18 includes the light source translation actuator 110, the light output controller 111, the focus controller 112, an irradiation direction controller 140 and the output port 113. The irradiation direction controller 140 is used only for controlling the irradiation direction, and may be provided just in front of the output port 113 or immediately after the output port 113.

Since the light may be applied from inclined direction to the photoresist-coated substrate having the photomask 31 mounted thereon, which is placed on the stage 21, by means of the irradiation direction controller 140, the stage 21 supported by the stage support 116 may be horizontally fixed. The light may be applied from two directions by maintaining the stage 21 horizontal when the stage 21 is rotated by 180° by means of the stage rotation actuator (not shown) in this configuration.

Further, the irradiation direction of the light may be variously controlled by a combined operation of the irradiation direction controller 140, the stage inclination actuator or stage swing actuator, and the stage rotation actuator.

Various mechanisms may be appropriately used for the stage rotation actuator and the sate swing actuator or stage inclination actuator. For example, a rotation control mechanism known as a four-axis automatic X-ray diffractometer may be used for the stage rotation actuator and the stage swing actuator. A goniometer head widely used for X-ray diffractometers such as the four-axis automatic X-ray diffractometer, a Weissenberg camera and a precession camera may be used for the stage inclination actuator. On the other hand, a mechanism for fixing the stage support 116 merely by inclining it at a given angle may be used without using any of the above-mentioned mechanisms.

An apparatus such as a stepping motor may be appropriately used for the driving system. An apparatus such as a personal computer having a processor, a memory device and an input-output device may be appropriately used for the control system.

Figure 19:
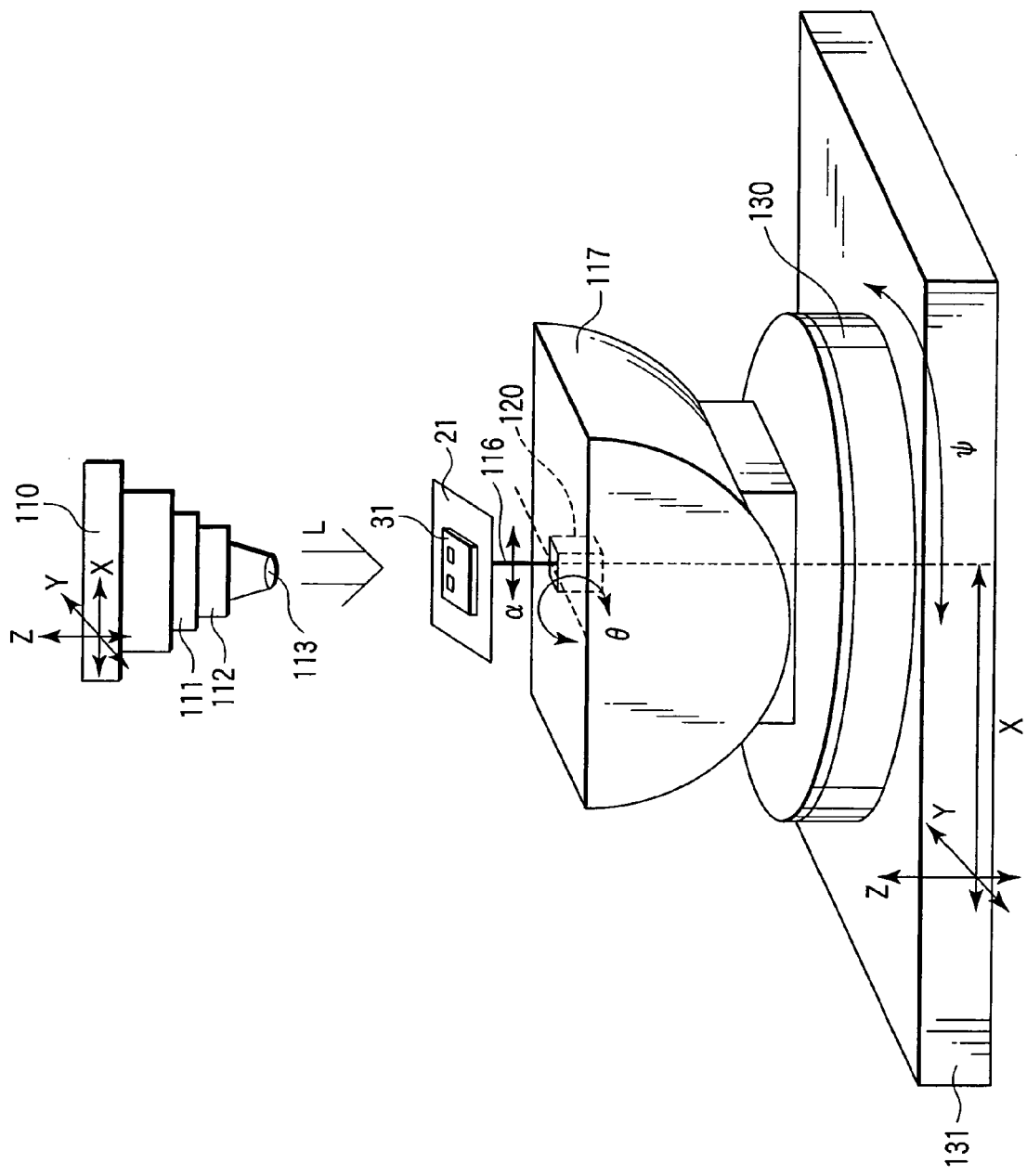
FIG. 19 shows a perspective view of an exposure apparatus provided with a stage inclination actuator, a stage swing actuator, a stage rotation actuator and a stage translation actuator.

FIG. 19 is a perspective view of an exposure apparatus provided with the stage inclination actuator 120, stage swing actuator 117, stage rotation actuator 130 and stage translation actuator 131. The irradiation direction controller 140 may be provided in the exposure optical system 119 in addition to these mechanisms. The irradiation direction and irradiation position of the light onto the photoresist-coated substrate having the photomask mounted thereon, which is placed on the stage 21, may be controlled in various ways by using these mechanisms together.

The exposure apparatus of the invention is not always required to have all of the stage inclination actuator 120, stage swing actuator 117, stage rotation actuator 130 and stage translation actuator 131. An exposure apparatus having the stage inclination actuator 120 and the stage rotation actuator 130, or an exposure apparatus having the stage swing actuator 117 and stage rotation actuator 130 may be freely designed.

Figure 20A:
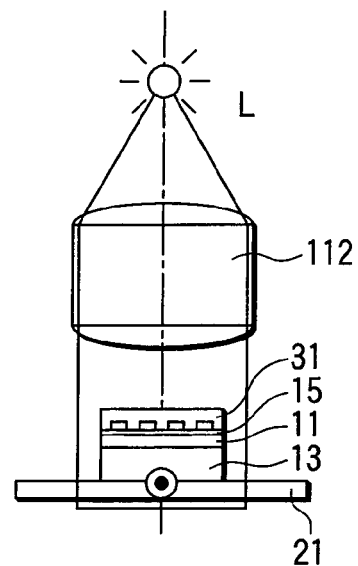
FIGS. 20A to 20C show schematic views illustrating the relation between the stage and the direction of light when the stage is inclined.
Figure 20B:
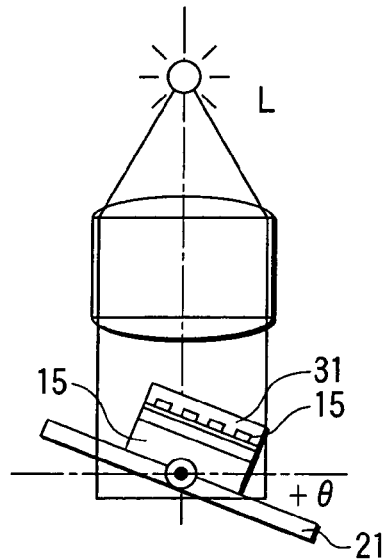
Figure 20C:
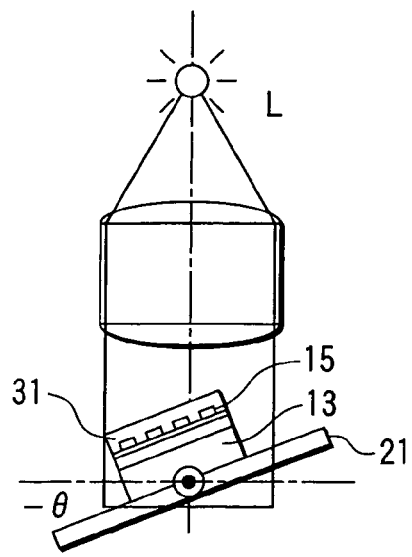

As shown in FIGS. 20A to 20C, the stage 21 may be inclined in plural directions relative to the irradiation direction of the light L by designing the stage 21 to be able to incline. The stage 21 is inclined by rotating the stage 21 around a rotation axis perpendicular to the irradiation direction of the light.

FIG. 20A shows the stage 21 at a horizontal position. FIG. 20B shows the stage 21 inclined at an angle +θ. FIG. 20C shows the stage 21 inclined at an angle −θ. The light may be symmetrically applied to the photoresist 11 by allowing the stage 21 to be inclined at the angles of ±θ.

The means for inclining the stage 21 may be either the stage swing actuator 117 shown in FIG. 14, or the stage inclination actuator 120 and stage support 116 shown in FIG. 15.

EXAMPLES

The microneedle patch manufactured by the invention was compared with the microneedle patch manufactured by a conventional technique.

The microneedle was manufactured as follows by the method of the invention. A photomask having plural island radiation shields was disposed on a negative photoresist coated on a substrate, and the photomask was integrated with the photoresist. Light was applied to the photoresist film from plural directions through the photomask and exposure and development were performed to manufacture master plates of the photoresist having recesses of triangular, square and round cone shapes, respectively. A metal inversion plate was manufactured from each of the master plate, a metal replication plate was manufactured from each of the inversion plate, and microneedles made of polylactic acid were manufactured from the replication plate.

For comparison, by using the conventional technique, silicon master plates having recesses of triangular, square and round cone shapes, respectively, were manufactured by dry etching of single crystalline silicon substrates using resist patterns as masks, a metal replication plate was manufactured from each of the silicon master plates, and microneedles made of polylactic acid were manufactured from the replication plate.

The surface roughness of the polylactic acid microneedle of the invention was compared with the surface roughness of the conventional polylactic acid microneedle.

A contact type surface roughness meter cannot be applied to the microneedle. Accordingly, surface roughness (Ra, Rz) was measured using a non-contact type three-dimensional profilometer.

Ra denotes an absolute value of a point projected from an average value, and Rz denotes an average of five highest ranking values of points projected from the average value.

The surface roughness of the polylactic acid microneedle manufactured by the method of the invention was as follows: Ra in the height direction was 0.5 µm and Ra in the circumference direction was 0.9 µm in the triangular cone microneedle; Ra in the height direction was 0.5 µm and Ra in the circumference direction was 0.8 µm in the square cone microneedle; and Rz in the height direction (corresponding to the irradiation direction of the light L in FIG. 7A) was 0.2 µm and Rz in the circumference direction (corresponding to the direction of rotation in FIG. 7A) was 1.0 µm in the round cone microneedle.

On the other hand, the surface roughness of the polylactic acid microneedle as a comparative product manufactured from the master plate of the single crystalline silicon was as follows: Ra in the height direction was 6.5 µm and Ra in the circumference direction was 5.9 µm in the triangular cone microneedle; Ra in the height direction was 8.5 µm and Ra in the circumference direction was 6.8 µm in the square cone microneedle; and Rz in the height direction was 5.2 µm and Rz in the circumference direction was 7.0 µm in the round cone microneedle.

The microneedle of the invention was excellent in surface smoothness with a surface roughness of 1 µm or less, although the surface roughness of the comparative microneedle manufactured by the conventional technique was 5 µm or more. Yield of the replication plate as well as peelability in forming the microneedle was very good in the invention.

The microneedle may be used as a tool for supplying drugs by coating the surface of the microneedle with, for example, nitroglycerin, isosorbide nitrate, estradiol, tulobuterol, nicotine, scorapon and clonidine hydrochloride. These drug components may be added to the material constituting the microneedle patch. An example of this application is a microneedle prepared from a mixture containing chitin/chitosan and a pharmaceutical composition.

The microneedle patch of the invention can be manufactured in large scale with a relatively simple manufacturing process, and has a sharp tip and smooth surface. Accordingly, the microneedle patch can be used in medical fields such as administration of drugs and sampling of blood, in the fields of micro-chemical analysis such as a liquid spray nozzle, and in industrial fields such as ink-jet printer nozzles.

Since the exposure apparatus of the invention can readily control a relative angle of inclination between the light irradiation direction and photoresist film with a simple construction, it may be used for manufacturing various structures such as a microneedle array.

What is claimed is:

1. A method of manufacturing a microneedle patch having a plurality of microneedles comprising:
    forming a photoresist film on a substrate;
    disposing a photomask having a plurality of island radiation shields each having a shape corresponding to a polygonal bottom face of each microneedle, on the photoresist film followed by integrating the photomask and the photoresist film;
    applying light from a light source to the photoresist film through the photomask from a plurality of inclined directions to selectively expose the photoresist film;
    developing the photoresist film to form a master plate having a plurality of recesses or projections corresponding to a plurality of microneedles;
    manufacturing a replication plate using the master plate; and
    molding a microneedle patch having a plurality of microneedles using the replication plate, each microneedle having a polygonal bottom face, inclined side walls, and a sharp tip.

2. The method according to claim 1, further comprising:
    manufacturing an inversion plate having an inversion pattern of the master plate from the master plate using a negative photoresist as the photoresist; and
    manufacturing a replication plate having an inversion pattern of the inversion plate from the inversion plate.

3. The method according to claim 1, further comprising:
    manufacturing a replication plate having an inversion pattern of the master plate from the master plate using a positive photoresist as the photoresist.

4. A microneedle patch manufactured by the method according to claim 1, wherein the microneedles are disposed on a patch substrate in parallel.

5. The microneedle patch according to claim 4, wherein the microneedle has a surface roughness of 5 µm or less.

6. The microneedle patch according to claim 4, wherein the shape of the microneedle is a combination of a cone and a trapezoidal cone having discontinuously changing diameters.

7. The microneedle patch according to claim 4, wherein the entire microneedles or a part of the microneedles are made of a biocompatible material.

* * * * *

UNITED STATES PATENT AND TRADEMARK OFFICE
CERTIFICATE OF CORRECTION

PATENT NO.         : 8,062,835 B2
APPLICATION NO.    : 12/379308
DATED              : November 22, 2011
INVENTOR(S)        : Takao Tomono Page 1 of 1

It is certified that error appears in the above-identified patent and that said Letters Patent is hereby corrected as shown below:

On the Title page: Item (54) and Column 1, Line 3-4, Title, delete "PATCH AND APPARATUS EXPOSURE APPARATUS" and insert -- PATCH MICRONEEDLE PATCH AND EXPOSURE APPARATUS --, therefor.

Signed and Sealed this
Fourth Day of September, 2012

David J. Kappos
*Director of the United States Patent and Trademark Office*